(12) United States Patent
Shanjani et al.

(10) Patent No.: US 12,390,307 B2
(45) Date of Patent: Aug. 19, 2025

(54) AUGMENTED REALITY ENHANCEMENTS FOR DENTAL PRACTITIONERS

(71) Applicant: Align Technology, Inc., San Jose, CA (US)

(72) Inventors: Yaser Shanjani, Milpitas, CA (US); Bruce Cam, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 338 days.

(21) Appl. No.: 17/882,371

(22) Filed: Aug. 5, 2022

(65) Prior Publication Data

US 2022/0370170 A1  Nov. 24, 2022

Related U.S. Application Data

(63) Continuation of application No. 17/188,436, filed on Mar. 1, 2021, now Pat. No. 11,419,701, which is a
(Continued)

(51) Int. Cl.
*G06T 19/00*  (2011.01)
*A61B 34/00*  (2016.01)
(Continued)

(52) U.S. Cl.
CPC .............. *A61C 7/002* (2013.01); *A61B 34/00* (2016.02); *A61B 90/361* (2016.02); *A61B 90/37* (2016.02);
(Continued)

(58) Field of Classification Search
CPC ....... A61C 7/002; A61C 7/146; A61C 9/0046; A61C 13/34; A61C 9/0053; A61B 34/00; A61B 90/361; A61B 90/37; A61B 2090/365; G02B 27/0172; G02B 27/017; G02B 2027/014; G02B 2027/0141; G02B 2027/0178; G02B 2027/0138; G06F 3/011; G06F 3/013; G06F 3/017; G06T 7/0012; G06T 7/60; G06T 19/006; G06T 2207/30036; G06T 2210/41
See application file for complete search history.

(56) References Cited

U.S. PATENT DOCUMENTS 10,342,638 B2 * 7/2019 Kitching ................ G16H 50/50
10,980,613 B2 * 4/2021 Shanjani ............ G02B 27/0172
(Continued)

*Primary Examiner* — Ming Y Hon
(74) *Attorney, Agent, or Firm* — Shay Glenn LLP

(57) ABSTRACT

Apparatuses and methods for performing orthodontic treatment planning are provided. Virtual/Augmented Reality devices can be used to virtually manipulate patient's teeth, modify virtual models of the patient's teeth, analyze the fit of a dental appliance on the patient's teeth, analyze the position of attachment sites for dental appliances, and provide overlays showing forces applied to the patient's teeth. The VR/AR devices can be used by physicians and/or the patient to provide and display treatment planning. In some examples, a length and/or angle of an elastic band or wire and one or more effective forces on a patient's teeth when a dental appliance is applied to the patient's teeth may be determined. A visual overlay graphically illustrating the one or more effective forces may be generated and displayed.

20 Claims, 12 Drawing Sheets

Developing Treatment Plan

Related U.S. Application Data continuation of application No. 16/231,906, filed on Dec. 24, 2018, now Pat. No. 10,980,613.

(60) Provisional application No. 62/612,308, filed on Dec. 29, 2017.

(51) Int. Cl.
<table>
<tr><td>A61B 90/00</td><td>(2016.01)</td></tr>
<tr><td>A61C 7/00</td><td>(2006.01)</td></tr>
<tr><td>A61C 7/14</td><td>(2006.01)</td></tr>
<tr><td>A61C 9/00</td><td>(2006.01)</td></tr>
<tr><td>A61C 13/34</td><td>(2006.01)</td></tr>
<tr><td>G02B 27/01</td><td>(2006.01)</td></tr>
<tr><td>G06F 3/01</td><td>(2006.01)</td></tr>
<tr><td>G06T 7/00</td><td>(2017.01)</td></tr>
<tr><td>G06T 7/60</td><td>(2017.01)</td></tr>
</table>

(52) U.S. Cl.
CPC ............ *A61C 7/146* (2013.01); *A61C 9/0046* (2013.01); *A61C 13/34* (2013.01); *G02B 27/0172* (2013.01); *G06F 3/011* (2013.01); *G06F 3/013* (2013.01); *G06F 3/017* (2013.01); *G06T 7/0012* (2013.01); *G06T 7/60* (2013.01); *G06T 19/006* (2013.01); *A61B 2090/365* (2016.02); *A61C 9/0053* (2013.01); *G02B 2027/014* (2013.01); *G02B 2027/0141* (2013.01); *G02B 27/017* (2013.01); *G02B 2027/0178* (2013.01); *G06T 2207/30036* (2013.01); *G06T 2210/41* (2013.01)

(56) References Cited

U.S. PATENT DOCUMENTS

| | | | |
|---|---|---|---|
| 11,297,285 B2* | 4/2022 | Pierce | A61C 1/084 |
| 2005/0186540 A1* | 8/2005 | Taub | G05B 19/0421 700/118 |
| 2006/0257815 A1* | 11/2006 | De Dominicis | A61C 7/00 433/24 |
| 2007/0184422 A1* | 8/2007 | Takahashi | H04N 7/181 348/E7.086 |
| 2008/0248443 A1* | 10/2008 | Chishti | G06T 17/00 433/24 |
| 2009/0074251 A1* | 3/2009 | Sears | G06T 7/246 382/106 |
| 2009/0148805 A1* | 6/2009 | Kois | A61C 13/0001 433/24 |
| 2010/0167225 A1* | 7/2010 | Kuo | A61C 7/002 702/137 |
| 2011/0091832 A1* | 4/2011 | Kim | B29C 64/00 700/119 |
| 2011/0104630 A1* | 5/2011 | Matov | A61C 9/004 703/1 |
| 2012/0003602 A1* | 1/2012 | Waldmeier | A61B 1/247 433/30 |
| 2013/0204599 A1* | 8/2013 | Matov | G16H 50/50 703/11 |
| 2014/0379356 A1* | 12/2014 | Sachdeva | A61C 7/002 705/2 |
| 2015/0079531 A1* | 3/2015 | Heine | A61C 7/08 433/19 |
| 2015/0142400 A1* | 5/2015 | Matov | G06F 30/20 345/420 |
| 2016/0128624 A1* | 5/2016 | Matt | A61C 19/045 600/301 |
| 2016/0220200 A1* | 8/2016 | Sandholm | A61B 5/4848 |
| 2017/0065379 A1* | 3/2017 | Cowburn | A61C 13/0004 |
| 2017/0265978 A1* | 9/2017 | Borotto | A61C 19/05 |
| 2018/0110590 A1* | 4/2018 | Maraj | A61C 7/002 |
| 2020/0005676 A1* | 1/2020 | Kubota | G09B 9/00 |
| 2022/0079714 A1* | 3/2022 | Paraketsov | G06T 17/20 |
| 2024/0257339 A1* | 8/2024 | Girardot | G06T 3/40 |

* cited by examiner

Developing Treatment Plan

Analyze Dental Appliance

Poor Fit

Good Fit

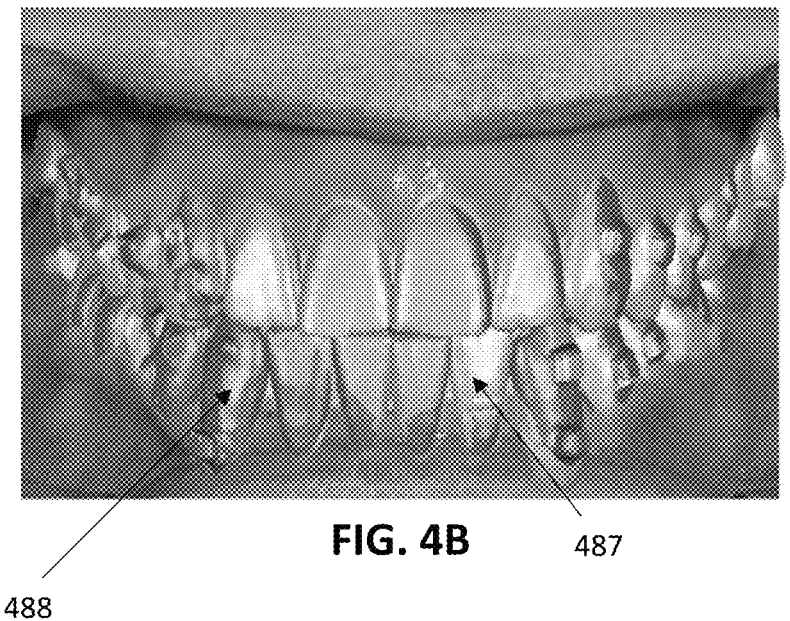

Receive (e.g., in a processor of the AR system) a first data set comprising a treatment plan for a patient's teeth 458.

Receive (receive, from an augmented reality system worn by a dental practitioner, an image data set comprising a representation of the patient's current teeth 460.

Compare the first data set to the image data set to determine one or more variations from the treatment plan 462.

Displaying the one or more variations on a visual display of the augmented reality system worn by the dental practitioner superimposed over a view of the patient's teeth 464.

FIG. 4C

Analyze Attachments

Display Forces on teeth

Forces and moment on wire-based dental appliance

Displaying VR to patient

AUGMENTED REALITY ENHANCEMENTS FOR DENTAL PRACTITIONERS

CROSS REFERENCE TO RELATED APPLICATIONS

This patent application is a continuation of U.S. patent application Ser. No. 17/188,436, filed on Mar. 1, 2021, titled "AUGMENTED REALITY ENHANCEMENTS FOR DENTAL PRACTITIONERS," now U.S. Pat. No. 11,419,701, which is a continuation of U.S. patent application Ser. No. 16/231,906, filed on Dec. 24, 2018, titled "AUGMENTED REALITY ENHANCEMENTS FOR DENTAL PRACTITIONERS," now U.S. Pat. No. 10,980,613, which claims priority to U.S. Provisional Patent Application No. 62/612,308, filed on Dec. 29, 2017, titled "AUGMENTED REALITY ENHANCEMENTS FOR DENTAL PRACTITIONERS," each of which is herein incorporated by reference in its entirety.

This patent may be related to one or more of: U.S. patent application Ser. No. 15/841,212, filed Dec. 13, 2017, titled "AUGMENTED REALITY PLANNING AND VIEWING OF DENTAL TREATMENT OUTCOMES," now U.S. Pat. No. 10,467,815; U.S. patent application Ser. No. 15/841,200, filed Dec. 13, 2017, titled "AUGMENTED REALITY ENHANCEMENTS FOR INTRAORAL SCANNING," now U.S. Pat. No. 10,695,150; U.S. patent application Ser. No. 15/841,196, filed Dec. 13, 2017, titled "AUGMENTED REALITY ENHANCEMENTS FOR DENTAL PRACTITIONERS," now U.S. Pat. No. 10,888,399; and U.S. patent application Ser. No. 15/803,718, filed Nov. 3, 2017, titled "METHODS AND APPARATUSES FOR DENTAL IMAGES," now U.S. Pat. No. 10,595,966, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

Augmented reality devices may provide additional information to users of the devices in the context of the surrounding real world environment. For example, an augmented reality device may provide audio, video, graphic, or other information to a user to supplement the information available in the real world environment.

SUMMARY OF THE DISCLOSURE

The present application relates to methods and apparatuses (e.g., devices and systems, including software) for using augmented reality or virtual reality systems to aid in orthodontic treatment planning.

The methods and apparatuses (e.g., systems, devices, etc.) described herein may be used to improve or assist in scanning of the teeth, tracking progress of an orthodontic treatment, forming or modifying an orthodontic treatment plan, and/or checking or modifying aspects of a treatment plan, including, but not limited to, placement and/or adjustment of attachments on a patient's teeth. In general, an augmented reality system, including in particular a system including one or more cameras on a wearable display (e.g., glasses, goggles, etc.) can be used to scan a patient's teeth, which may determine the position and/or orientation of the patient's teeth. The augmented reality system may therefore provide real-time scanning (including 3D imaging information) that may provide image data of the patient's teeth. This image data may include information about the position and orientation of the patient's individual teeth, and orthodontic components (e.g., aligners, palatal expanders, attachments, etc.) on the teeth, which may be compared with expected values from one or more treatment plans. This information may be interpreted in light of a more detailed 3D scan (e.g., using an intraoral scanner), without requiring the use of an intraoral scanner. In some variations a digital model of the patient's teeth may be used to interpret the augmented reality system images (e.g., the image data of the patient's current teeth, e.g., current dental arch(es)). The digital model may be prepared from an intraoral scanner. Thus, the methods and apparatuses described herein may assist in the analysis of a treatment plan at the start, finish or during a mid-treatment period, without requiring a full scan of the teeth using more complex intraoral scanning. These methods and systems may or additionally or alternatively be used to enhance a virtual reality display that a dental practitioner (e.g., dentist, orthodontist, dental technician, etc.) may customize for display to a patient (including in real time).

Thus, described herein are augmented reality (AR) and/or virtual reality (VR) methods and apparatuses (e.g., systems) to evaluate an orthodontic treatment plan. As described in detail below, such systems may be configured to show deviation(s) from current tooth position and/or orientation (angle, rotation, etc.) from one or more stages of a treatment plan.

The AR and/or VR systems described herein may alternatively or additionally be configured to review the position of and/or force(s) on one or more attachments on the patient's teeth. These systems may be configured to check the attachments at either the start of treatment (e.g., to show deviation of attachment positons from their intended position, and/or to describe forces on the one or more attachments) and/or during ongoing treatment (e.g., checking to be sure that the attachments are still present, and/or to describe forces on the one or more attachments).

The AR and/or VR systems described herein may be configured to estimate and/or display force(s) on the teeth and/or dental appliance and/or attachment(s) on the teeth. In some variations the AR and/or VR system may be configured to estimate and/or display the forces on the teeth and/or attachments when the patient is wearing an orthodontic appliance (e.g., an aligner, palatal expander, etc.). In some embodiments, the AR and/or VR systems described herein may be configured to determine how well a dental appliance (e.g., an aligner) fits a patient.

The methods and apparatuses may also be configured to include a slaved patient-wearable virtual reality display that displays a subset of the information displayed on a master dental professional-worn augmented reality display; the dental professional may control the slaved patient-wearable virtual reality display, including selecting the subset of information to be displayed. The slaved patient-wearable virtual reality display may show the image of the patient's teeth from the perspective of the dental professional, onto which is overlaid a subset of the augmented reality information that is shown on the master physician-wearable virtual reality device (e.g., highlighting teeth, movements, caries, etc.).

The methods and apparatuses described herein may also or alternatively be used to help design and/or modify a treatment plan. For example, an AR and/or VR system may be used to allow the dental professional to select one or more teeth to move, and to virtually move the one or more teeth to a final position and/or one or more intermediate (e.g., key) positions.

For example, described herein are methods of performing orthodontic treatment planning using augmented reality/virtual reality. Any of these methods may include: receiving, with a an augmented reality device (including a processor), a virtual model of a patient's teeth representing a dental arch, capturing, e.g., with the processor or other portion of the augmented reality device, image data of the patient's teeth, identifying, with the processor, a virtual selection by a user of at least one tooth from the virtual model and image data, generating, with the augmented reality device, a visual overlay identifying the virtual selection, outputting the visual overlay to a display of the augmented reality device, wherein the visual overlay is superimposed over a view of the patient's teeth identifying a virtual manipulation by the user of the virtual selection, wherein the virtual manipulation modifies the virtual model, generating an updated visual overlay corresponding to the virtual manipulation, outputting the updated visual overlay to the display, wherein the visual overlay is superimposed over the view of the patient's teeth.

Any of the steps of these methods described herein may be performed by the augmented reality device, including a processor of an augmented reality device. In some variations, a separate processor may be used (e.g., separate from the augmented reality device).

In any of the steps including manipulation of the at least one tooth, the manipulation may be real or virtual. F or example, "real" manipulation may include contacting a patient's tooth with a tool, such as a dental/orthodontic tool, that includes a sensor that may indicate which tooth is selected and or what manipulations (e.g., application of force, rotation, including vector—e.g., magnitude and direction—is being applied). The tool may then create virtual information that may be overlaid as described. For example, an image processor of an augmented reality (AR) or virtual reality (VR) system can detect a real manipulation (probing of tooth) that could then be visualized in a virtual way. The display may be virtually exaggerated and displayed on the selected tooth, e.g., an image of the selected tooth and/or an overlay onto the selected actual tooth. For example, a tool may include one or more sensors (force sensor, tri-axial sensor(s), etc.). Alternatively the manipulation may be virtual.

For example, the processor may recognize a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying the forces acting on the teeth.

As further described herein, the virtual manipulation may comprise moving the at least one tooth or rotating the at least one tooth.

Alternatively or additionally, the method may further comprise receiving an input from the user corresponding to the virtual manipulation, wherein the user is constrained in making a virtual manipulation based on a change in position of one or more teeth in the virtual model.

A method of performing orthodontic treatment planning is also provided, comprising generating a visual overlay comprising a virtual model of a dental arch, outputting the visual overlay to an augmented reality display, receiving user input based on a user interaction with at least one tooth of the virtual model of the dental arch, wherein the user input modifies the virtual model of the dental arch, determining a treatment plan for the dental arch based on the user input, and generating an updated visual overlay, wherein the updated visual overlay comprises a view of the dental arch after implementing the treatment plan.

The step of receiving user input based on a user interaction may be based on user interaction with at least one tooth of the virtual model of the dental arch or a patient's real dental arch.

For example, a user input may be a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying force vectors resulting from the treatment plan.

As further described herein, the virtual manipulation may comprise moving the at least one tooth or rotating the at least one tooth. Additionally, the user interaction may include adding a virtual attachment to the at least one tooth. The methods described herein may further include identifying if the virtual attachment is improperly placed.

Alternatively or additionally, the method may further comprise receiving an input from the user corresponding to the virtual manipulation, wherein the user is constrained in making a virtual manipulation based on a change in position of one or more teeth in the virtual model.

A system comprising an augmented reality display a memory device and a processing device operatively coupled to the memory device is further provided, the processing device configured to generate a visual overlay comprising a virtual model of a dental arch, output the visual overlay to the augmented reality display, receive user input based on a user interaction with at least one tooth of the virtual model of the dental arch (and/or of the patient's actual/real tooth), wherein the user input modifies the virtual model of the dental arch, determine a treatment outcome for the dental arch based on the user input; generate an updated visual overlay, wherein the updated visual overlay comprises a view of the dental arch after implementing the treatment outcome.

In general, any of these apparatuses (e.g., systems) may include an processor (and/or image processing sensors) and/or one or more controllers. Examples of such system architectures are provided herein and may generally include a processing unit, a memory unit, etc.

The step of receiving user input based on a user interaction with at least one tooth of the virtual model of the dental arch or a patient's real tooth may be based on receiving user input from one or more sensor inputs, e.g., on a user-held device, such as a probe or dental tool that includes one or more sensors, as mentioned above. Hand gestures or verbal commands may be used in addition or alternatively. The system may generally include an optical control sensors. Thus, any of the apparatuses (e.g., systems) described herein may include one or more dental tools with a probe or sensor that feeds information to the AR/VR system. The data from the tool may be received and used by the apparatus/system.

For example, a user input may be a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying force vectors resulting from the treatment plan.

As further described herein, the virtual manipulation may comprise moving the at least one tooth or rotating the at least one tooth. Additionally, the user interaction may include adding a virtual attachment to the at least one tooth. The methods described herein may further include identifying if the virtual attachment is improperly placed.

Alternatively or additionally, the method may further comprise receiving an input from the user corresponding to the virtual manipulation, wherein the user is constrained in making a virtual manipulation based on a change in position of one or more teeth in the virtual model.

Also described herein are methods of evaluating the fit of an orthodontic appliance such as an aligner. Any of these methods may include: capturing, with a processor of an augmented reality device, image data of a patient's teeth and of an appliance placed on the patient's teeth, identifying from the image data, with the processor, an error condition indicative of improper appliance fit on the patient's teeth, generating, with the processor, a visual overlay identifying the error condition, outputting the visual overlay to a display of the augmented reality device, wherein the visual overlay is superimposed over a view of the patient's teeth and of the appliance placed on the patient's teeth.

In general, the methods described herein may determine (e.g., create) one or more error conditions from just image data of the patient's teeth (or image data and additional sensor data), knowing what their expected position of teeth is going to be. For example, if the patient is in for a check-in appointment, and image data of the patient's teeth and treatment plan are provided to the system, the system may detect deviation from the treatment plan. The patient's dental health may be assessed by identifying/reviewing the error condition, including displacement of teeth under the input load. The apparatus may determine or detect a measure of tooth movement, force on the teeth, etc., and may precisely determine actual tooth movement. If the tooth movement is outside of an expected range, the apparatus may determine that the tooth movement is unhealthy and may flag/indicate this. This may be done based on predicted tooth movement as well/alternatively. The error condition may be determined between, for example, an aligner and an attachment on the tooth. Thus, the error condition may indicate an error in the position of the attachment; predicted fit may be estimated/determined by looking at the attachment on the tooth. The expected positon, size, and/or geometry of the attachment may be compared to the actual attachment, or the prescribed attachment from the treatment plan and used to generate an error condition.

In any of these methods and apparatuses, multiple error conditions may be simultaneously or sequentially presented (e.g., by AR/VR display).

As further described herein, the error condition can include a gap between the appliance and its corresponding tooth or a deformation of the appliance beyond a deformation threshold.

Alternatively or additionally, the method may further include displaying the error condition in a color. The visual overlay may be outputted to a display device worn on or over the user's head.

According to the present disclose, identifying the error condition may comprise determining, using an image of the orthodontic appliance, a region of poor fit between the patient's teeth and the orthodontic appliance. Identifying the error condition can also comprise estimating forces acting on the patient's teeth and indicating on the visual overlay where the forces exceed a threshold value. Estimating the forces acting on the patient's teeth can comprise identifying one or more elastics attached to the dental appliance.

As further described herein, a system is provided comprising an augmented reality display, a memory device, and a processing device operatively coupled to the memory device, the processing device configured to capture, with a processor of an augmented reality device, image data of a patient's teeth and of an aligner placed on the patient's teeth, identify from the image data, with the processor, an error condition indicative of improper aligner fit on the patient's teeth, generate, with the processor, a visual overlay identifying the error condition, output the visual overlay to a display of the augmented reality device, wherein the visual overlay is superimposed over a view of the patient's teeth and of the aligner placed on the patient's teeth.

As further described herein, the error condition can include a gap between the appliance and its corresponding tooth or a deformation of the appliance beyond a deformation threshold.

This disclosure further provides a method of evaluating attachment sites for an orthodontic appliance, such as an aligner, comprising capturing, with a processor of an augmented reality device, image data of a patient's teeth including one or more attachment sites for an orthodontic appliance attached to the patient's teeth, identifying from the image data, with the processor, an error condition indicative of improper position or orientation of one or more attachment site on the patient's teeth, generating, with the processor, a visual overlay identifying the error condition, outputting the visual overlay to a display of the augmented reality device, wherein the visual overlay is superimposed over a view of the patient's teeth and of the one or more attachment sites on the patient's teeth.

The method may further comprise receiving a target location for each of the one or more attachment sites on the patient's teeth.

Alternatively or additionally, the error condition may comprise a location of the attachment site that is different from a target location, or an orientation of the attachment site that is different from a target orientation.

According to the present disclosure, outputting the visual overlay can comprise displaying the error condition in a color and/or with an alphanumeric indicator, and outputting the visual overlay to a display device worn on or over the user's head.

Methods of evaluating an orthodontic treatment are also described. For example, these methods may include capturing, with a processor of an augmented reality device, image data of a patient's teeth, determining one or more effective forces on the patient's teeth when a dental appliance is applied to the patient's teeth, generating, with the processor, a visual overlay graphically illustrating the one or more effective forces, outputting the visual overlay to a display of the augmented reality device, wherein the visual overlay is superimposed over a view of the patient's teeth and of the elastic band or wire placed on the patient's teeth.

As further described herein, generating the visual overlay can comprise representing the one or more effective forces as an arrow, an alphanumeric value, or as a color. The one or more effective forces on the patient's teeth can be determined by determining a length and/or angle of an elastic band or wire on the dental appliance.

Determining the one or more effective forces on the patient's teeth can comprise determining a moment or torque on one or more teeth.

As further described herein, the method can include capturing the image of the patient's teeth when the dental appliance is worn by the patient, capturing the image of the patient's teeth when the dental appliance is not being worn by the patient and receiving a virtual model of the dental appliance.

For example, described herein are methods of evaluating an orthodontic treatment that may include: capturing, with a processor of an augmented reality device, image data of a patient's teeth; determining one or more effective forces on the patient's teeth when a dental appliance is applied to the patient's teeth; generating, with the processor, a visual overlay graphically illustrating the one or more effective forces; and outputting the visual overlay to a display of the augmented reality device, wherein the visual overlay is superimposed over a view of the patient's teeth and of the dental appliance placed on the patient's teeth.

The appliance may be any appliance, including elastics that may be worn to apply force to the teeth and/or wires. Other appliances may include aligners (e.g., having a bite ramp and/or other force-applying region), palatal expanders, and the like.

Forces on the teeth and/or apparatus may be determined and displayed by the AR/VR apparatuses as part of any of these methods. For example, force may be shown by force overlays. Types of force overlays that may be applied may include overlays showing the forces predicted, estimated or actually applied (measured) on the teeth and/or appliance. Force overlays may be shown graphically with or without text, including showing vectors (e.g., indicating direction and/or magnitude, including rotational forces (torque, etc.). In some variations the force overlay maybe shown without requiring other components of an AR/VR system, including just providing an annotated description/image, or listing of the forces predicted, estimated or actually applied. The display of such force maps may be particularly helpful to a user, adding information/data that the user (e.g., dental practitioner, physician, etc.) may use to form or modify a treatment plan. This information may be displayed in real time (e.g., instantaneously), effectively augmenting the data of the user.

In some variations the data (force data) may correspond to data from a dental probe or other dental device. For example, force applied by the dental probe may be shown in a realistic or exaggerated display, indicating potential tooth movements and their consequences, including consequence of a dental plan. For example, image data may be combined with input data (e.g., from a dental probe) and shown in the display either as force data or as movements due to applied force.

In some variations, the virtual data may highlight/exaggerate features from the scan of the patient's teeth that indicate dental issues (e.g., tartar, etc.) and the dental probe may indicate the interaction with such features. For example, tartar of other elements of the teeth may be shown in color on a representation of the teeth and a sensor on a dental tool (e.g., pick, probe, etc.) may show the interaction of the tool with the highlighted/colored feature(s), including showing (in a patient view) the removal (actual, simulated and/or predicted) removal.

Also described herein are systems comprising an augmented reality display, a memory device, and a processing device operatively coupled to the memory device, the processing device to capture, with a processor of an augmented reality device, image data of a patient's teeth and of an elastic band or wire placed on the patient's teeth, determine from the image data, with the processor, a length and/or angle of the elastic band or wire, and an effective force on a center of rotation of at least one of the patient's teeth resulting from the elastic band or wire, generate, with the processor, a visual overlay identifying the effective force, output the visual overlay to a display of the augmented reality device, wherein the visual overlay is superimposed over a view of the patient's teeth and of the elastic band or wire placed on the patient's teeth.

Also described herein are methods of displaying an orthodontic procedure. Any of these methods may include: capturing, with a processor of an augmented reality device, image data of a patient's teeth, generating, with the processor, a first visual overlay graphically illustrating one or more features of the patient's teeth and/or information about the patient's teeth, generating, from the first visual overlay, a second visual overlay comprising a subset of the one or more features of the patient's teeth and/or information about the patient's teeth, outputting the first visual overlay to a first, user-worn, display of the augmented reality device, wherein the first visual overlay is superimposed over a view of the patient's teeth, and outputting the second visual overlay to a second user-worn display of the augmented reality device, which may be superimposed over the view of the patient's teeth.

As further described herein, outputting the second visual overlay can be done concurrently with outputting the first visual overlay, or can be done after a time delay from outputting the first visual overlay.

Alternatively, generating the first visual overlay can comprise graphically illustrating movement of one or more of the patient's teeth, or indicating one or more dental carries on the patient's teeth.

In general, the methods and apparatuses described herein may display 'slave' visual outputs (visual overlay) that may be displayed as an overlay on an image of the patient's teeth (as seem by the 'master' device, e.g., worn by the dental professional), or may be viewed just an overlay animation without the 'real' image of the teeth. The slave display may be viewed by an assistant and/or by the patient. In some example, the patient may view a patient-specific display. The master display may be modified by the primary user (e.g., dental professional) for display in real time or with a time delay to the slave display(s). For example, the master user may modify the display to highlight a region or to include an additional image of a region for display to the slave display. As mentioned, the slave display may be transmitted and viewed by a patient, by another dental professional (doctor, orthodontist, etc.) or to an assistant. For example, the slave display may be viewed by another dental professional that may offer advice or assistance, etc. for training or for handling more difficult cases. In some variations, the display may be broadcast to one or more external sources to get live feedback/advice (e.g., on how to handle the case). This method (or an apparatus configured to perform such a method) may be used, for example, for virtual training and/or for treatment planning. The dental professional may download a virtual patient and be shown a preview of aligner treatment on the virtual patient. In some variations these methods and apparatuses may provide information on soft tissue, such as gingiva, including the effect of dental treatment (actual or planned) on impingement or other treatment of the soft tissue. This may be particularly helpful for treatment of palatal expanders, for example.

As mentioned above, the methods and apparatuses described herein may be used to provide one or more AR and/or VR systems to analyze treatment progress, e.g., to analyze how an orthodontic treatment plan is progressing. For example, a method of evaluating an orthodontic treatment may include: receiving, in a processor, a first data set comprising a treatment plan for a patient's teeth; receiving, from an augmented reality system worn by a dental practitioner, an image data set comprising a representation of the patient's current teeth; comparing the first data set to the image data set to determine one or more variations from the treatment plan; displaying the one or more variations on a visual display of the augmented reality system worn by the dental practitioner superimposed over a view of the patient's teeth.

Any of these methods may be methods of evaluating an orthodontic treatment using an augmented reality system worn by a dental practitioner, and may include: receiving, in a processor of the augmented reality system, a first data set comprising a treatment plan for a patient's teeth; receiving from the augmented reality system, an image data set comprising a representation of the patient's current teeth; determining the positions and orientations of one or more of the patient's teeth relative to the patient's dental arch from the image data set; comparing the positions and orientations of the one or more of the patient's teeth relative to the patient's dental arch with the treatment plan to determine one or more variations from the treatment plan; and displaying the one or more variations on a visual display of the augmented reality system worn by the dental practitioner superimposed over a view of the patient's teeth.

Any of these methods may also include receiving a virtual model of a patient's teeth representing a dental arch, and further wherein determining the positions and orientations of one or more of the patient's teeth relative to the patient's dental arch from the image data set comprises matching the image data of the patient's teeth to a virtual model of the patient's teeth to identify corresponding teeth from the image data of the patient's teeth.

The virtual model of the patient's teeth may include a scan taken prior to the start of the orthodontic treatment.

Displaying the variations may comprise displaying a color on the view of the patient's teeth and/or an alphanumeric indicator and/or an outline or partial outline (highlighting) of the patient's teeth.

Any of these methods may also include identifying a stage of the treatment plan most closely corresponding to an arrangement of the patient's current teeth and wherein comparing the first data set to the image data set comprises comparing the stage of the treatment plan most closely corresponding to the arrangement of the patient's current teeth with the image data set to determine one or more variations. For example, identifying the stage of the treatment plan may comprise receiving the stage from the dental practitioner. Identifying the stage of the treatment plan may comprise identifying the stage with a lowest value for the one or more variations.

Comparing the first data set to the image data set may comprise comparing each stage of the treatment plan of the first data set to the image data set and further wherein displaying the one or more variations comprises displaying the one or more variations specific to each stage of the treatment plan.

The one or more variations may comprise one or more of: a difference in a tooth position relative to the patient's dental arch between a tooth of the patient's current teeth and a corresponding position of the tooth in a stage of the treatment plan from the first data set; a difference in an angle of the tooth relative to the patient's dental arch of the patient's current teeth and a corresponding angle of the tooth in a stage of the treatment plan of the first data set; and a difference in rotational position relative to the patient's dental arch of a tooth between a tooth of the patient's current teeth and a corresponding rotational position of the tooth in a stage of the treatment plan of the first data set.

Also described herein are systems for performing any of these methods, including, for example, a system comprising: an augmented reality display; one or more processors; a memory coupled to the one or more processors, the memory configured to store computer-program instructions, that, when executed by the one or more processors, perform a computer-implemented method comprising: receiving, in a processor, a first data set comprising a treatment plan for a patient's teeth; receiving, from an augmented reality system worn by a dental practitioner, an image data set comprising a representation of the patient's current teeth; comparing the first data set to the image data set to determine one or more variations from the treatment plan; displaying the one or more variations on a visual display of the augmented reality system worn by the dental practitioner superimposed over a view of the patient's teeth.

As described above, also described herein are AR and/or VR methods and apparatuses for analyzing attachments. In general an attachment may be a polymeric, metal and/or ceramic attachment that is bonded to a patient's tooth to help engage with a dental appliance (e.g., aligner, etc.) to help secure it in position. The AR and/or VR methods and apparatuses may determine the position and/or orientation of one or more appliances, determine and display forces acting on them, and or determine and display deviation from an intended position of the one or more appliances. For example, a method of evaluating attachments for an orthodontic appliance may include: capturing, with an augmented reality system including a wearable display worn by a dental practitioner, image data of a patient's teeth including one or more attachments for an orthodontic appliance configured to be attached to the patient's teeth; identifying from the image data, with the processor, an error condition indicative of improper position or orientation of the one or more attachments on the patient's teeth; generating a visual overlay identifying the error condition; and outputting the visual overlay to the wearable display worn by the dental practitioner, wherein the visual overlay is superimposed over a view of the patient's teeth and of the one or more attachments on the patient's teeth.

A method of evaluating attachments for an orthodontic appliance may include: capturing, with an augmented reality system including a wearable display worn by a dental practitioner, image data of a patient's teeth including one or more attachments for an orthodontic appliance attached to the patient's teeth; identifying from the image data, with the processor one or more of: forces acting on the one or more attachments, and an error condition indicative of improper position or orientation of the one or more attachments on the patient's teeth; generating a visual overlay identifying one or more of: the forces acting on the one or more attachments and the error condition; and outputting the visual overlay to the wearable display worn by the dental practitioner, wherein the visual overlay is superimposed over a view of the patient's teeth and of the one or more attachments on the patient's teeth.

Capturing be performed at the start of an orthodontic treatment and/or during an ongoing orthodontic treatment (e.g., at or between any of the stage of an orthodontic treatment, and/or at the end of the orthodontic treatment.

Any of these methods may include receiving a target location for each of the one or more attachments on the patient's teeth. Any of these methods may include receiving one or more of: a target location, position, size, shape, or orientation for each of the one or more attachments on the patient's teeth.

The error condition may indicate a difference in the location of the attachment that is different from a target attachment site location and/or a difference in the rotation of the attachment relative to a target attachment orientation (e.g., the error condition may comprise an orientation of the attachment that is different from a target orientation) and/or a missing attachment (e.g., the error condition may comprise one or more missing attachments).

In any of these methods, outputting the visual overlay may comprise displaying the error condition in a color and/or with an alphanumeric indicator. In some variations, outputting the visual overlay to a display of the augmented reality device may comprise outputting the visual overlay to a plurality of displays concurrently.

Also described herein are systems for performing any of these methods. For example, a system for evaluating attachments for an orthodontic appliance may include: a wearable augmented reality display; one or more processors; a memory coupled to the one or more processors, the memory configured to store computer-program instructions, that, when executed by the one or more processors, perform a computer-implemented method comprising: capturing image data of a patient's teeth including one or more attachment sites for an orthodontic appliance attached to the patient's teeth; identifying from the image data, with the processor, an error condition indicative of improper position or orientation of one or more attachments on the patient's teeth; generating a visual overlay identifying the error condition; outputting the visual overlay to the wearable augmented reality display to display the visual overlay superimposed over a view of the patient's teeth and of the one or more attachments on the patient's teeth.

As mentioned above, also described herein are methods and apparatuses for estimating and displaying forces on the teeth and/or dental appliance and/or attachments. For example, described herein are methods of evaluating an orthodontic treatment comprising: capturing, with a processor of an augmented reality device, image data of a patient's teeth; determining one or more effective forces on the patient's teeth when a dental appliance is applied to the patient's teeth; generating a visual overlay graphically illustrating the one or more effective forces; and outputting the visual overlay to a display of the augmented reality device worn by a dental practitioner, wherein the visual overlay is superimposed over a view of the patient's teeth and of the dental appliance placed on the patient's teeth.

The dental appliance may include an elastic band or wire.

In any of these methods, generating the visual overlay may comprise representing the one or more effective forces as an arrow. Generating the visual overlay may comprise representing the one or more effective forces as an alphanumeric value. Generating the visual overlay may comprise representing the one or more effective forces as a color. Any of these method may include determining one or more effective forces on the patient's teeth by determining a moment or torque on one or more teeth.

Capturing the image of the patient's teeth may comprise capturing the image of the patient's teeth when the dental appliance is worn by the patient. For example, capturing the image of the patient's teeth may comprise capturing the image of the patient's teeth when the dental appliance is not being worn by the patient; further comprising receiving a virtual model of the dental appliance.

In some variations, determining one or more effective forces on the patient's teeth may comprise determining a length and/or angle of an elastic band or wire on the dental appliance.

Also described herein are systems comprising: an augmented reality display; one or more processors; and a memory coupled to the one or more processors, the memory configured to store computer-program instructions, that, when executed by the one or more processors, perform a computer-implemented method comprising: capturing, with a processor of an augmented reality device, image data of a patient's teeth and of an elastic band or wire placed on the patient's teeth; determining from the image data, with the processor, a length and/or angle of the elastic band or wire, and an effective force on a center of rotation of at least one of the patient's teeth resulting from the elastic band or wire; generating, with the processor, a visual overlay identifying the effective force; and outputting the visual overlay to a display of the augmented reality device, wherein the visual overlay is superimposed over a view of the patient's teeth and of the elastic band or wire placed on the patient's teeth.

As mentioned above, also described herein are augmented reality and/or virtual reality systems and methods in which a dental professional master AR device may control operation of a slave patient-worn display (e.g., VR) device. These apparatuses may be used as part of an orthodontic procedure. For example, a method of displaying an orthodontic procedure, the method comprising: capturing, with a processor of an augmented reality system, image data of a patient's teeth; displaying, on a user augmented reality display device worn by a dental practitioner, a first visual overlay based on the image data of the patient's teeth, the first visual overlay graphically illustrating one or more of: features of the patient's teeth an information about the patient's teeth, wherein the first visual overlay is superimposed over a view of the patient's teeth; adjusting, by the dental practitioner, the first visual overlay, wherein the dental practitioner interactively engages with the first visual overlay; and displaying, on a patient display device worn by a patient, a second visual overlay comprising a subset of the one or more of: features of the patient's teeth and/or information about the patient's teeth, wherein the second visual overlay is superimposed over the view of the patient's teeth, wherein the dental practitioner controls the display of the second visual overlay.

For example, a method of displaying an orthodontic procedure, the method comprising: capturing, with an augmented reality system, image data of a patient's teeth; generating, from the image data, a first visual overlay graphically illustrating one or more of: one or more features of the patient's teeth, and information about the patient's teeth; outputting the first visual overlay to a user augmented reality display device worn by a dental practitioner, wherein the first visual overlay is superimposed over a view of the patient's teeth; generating, from the first visual overlay, a second visual overlay comprising a subset of the one or more of: features of the patient's teeth and/or information about the patient's teeth, wherein the dental practitioner modifies content from the first visual overlay to form the second visual overlay; and displaying, on a patient display device worn by a patient, the second visual overlay, wherein the second visual overlay comprises a representation of one or more of the patient's teeth.

Any of these methods may include interactively engaging with the first visual overlay by the dental practitioner, wherein the dental practitioner performed one or more of: moving, highlighting, or modifying the one or more of: features of the patient's teeth an information about the patient's teeth, wherein the first visual overlay is superimposed over a view of the patient's teeth.

These methods may also or alternatively include forming the second visual overlay by receiving, from the dental practitioner, the subset of the one or more of: features of the patient's teeth and/or information about the patient's teeth.

Outputting the second visual overlay may be done concurrently with outputting the first visual overlay. Displaying the second visual overlay may be done after a time delay from outputting or displaying the first visual overlay. Generating the first visual overlay may comprise generating a first visual overlay graphically illustrating movement of one or more of the patient's teeth. In some variations, generating the first visual overlay comprises indicating one or more dental carries on the patient's teeth. Any of these methods may include generating the second visual overlay by receiving modifications to the first visual overlay from dental practitioner.

Displaying the second visual overlay to a patient display device may comprise displaying the second visual overlay superimposed over a view of the patient's teeth.

As mentioned above, also described herein are AR and/or VR apparatuses and methods of using them for orthodontic treatment planning. For example, a method of performing orthodontic treatment planning may include: receiving a virtual model of a patient's teeth representing a dental arch; capturing, with an augmented reality system, image data of the patient's teeth; matching the virtual model of the patient's teeth to the image data of the patient's teeth to identify corresponding teeth from the image data of the patient's teeth; collecting, with the augmented reality system, a selection by a user of at least one tooth while capturing image data of the patient's teeth; generating, with the augmented reality system, a visual overlay identifying the selected at least one tooth; outputting the visual overlay to a display of the augmented reality system, wherein the visual overlay is superimposed over a view of the patient's teeth; receiving, in the augmented reality system, a translation of the selected at least one tooth by the user, wherein the translation modifies one or more of tooth angle relative to the patient's dental arch and tooth position relative the dental arch; updating the visual overlay to include the translation; modifying a target tooth virtual model of the patient's teeth to include the translation of the selected at least one tooth; and transferring the target tooth virtual model to a treatment plan generator to generate an orthodontic treatment plan. The augmented reality system may recognize a hand gesture of the user to identify the selection by the user of at least one tooth while capturing image data of the patient's teeth.

In some variations, the visual overlay comprises a visual outline of the at least one tooth. For example, the visual overlay may comprise shading or coloring of the at least one tooth. Receiving the translation may comprise sensing contact between a tooth of the patient and a dental tool comprising a sensor. The translation may comprise virtually moving the at least one tooth relative to the patient's dental arch. The translation may comprise virtually rotating the at least one tooth relative to the patient's dental arch.

Any of these methods may include repeating the steps of collecting, generating, outputting, receiving, updating and modifying to allow the user to select and adjust different target teeth.

For example, a method of performing orthodontic treatment planning may include: generating a visual overlay comprising a virtual model of a dental arch; outputting the visual overlay to an augmented reality display; receiving user input based on a user interaction with at least one tooth of the virtual model of the dental arch or a patient's real dental arch, wherein the user input modifies the virtual model of the dental arch; determining a treatment plan for the dental arch based on the user input; and generating an updated visual overlay, wherein the updated visual overlay comprises a view of the dental arch after implementing the treatment plan. The user input may comprise a hand gesture. The user input may comprise contact between a tooth of the patient and a dental tool comprising a sensor.

The visual overlay may comprises a visual outline of at least one tooth. The visual overlay may comprises shading or coloring of the at least one tooth.

The user interaction may comprises moving the at least one tooth. The user interaction may comprise rotating the at least one tooth. In some variations, the user interaction comprises adding a virtual attachment to the at least one tooth.

Any of these methods may include identifying if the virtual attachment is improperly placed.

The updated visual overlay may include force vectors resulting from the treatment plan.

Also described herein are systems for performing any of these methods. For example a system may include: an augmented reality display; one or more processors; and a memory coupled to the one or more processors, the memory configured to store computer-program instructions, that, when executed by the one or more processors, perform a computer-implemented method comprising: generating a visual overlay comprising a virtual model of a dental arch; outputting the visual overlay to the augmented reality display; receiving user input based on a user interaction with at least one tooth of the virtual model of the dental arch or a patient's real tooth, wherein the user input modifies the virtual model of the dental arch; determining a treatment outcome for the dental arch based on the user input; generating an updated visual overlay, wherein the updated visual overlay comprises a view of the dental arch after implementing the treatment outcome.

As described above, also described herein are AR and/or VR methods and apparatuses for analyzing the fit of one or more orthodontic appliances on a patient's teeth. For example, described herein are methods of evaluating fit of an orthodontic appliance, comprising: receiving an image data of an appliance placed on the patient's teeth; identifying from the image data, using an augmented reality system, an error condition indicative of improper appliance fit on the patient's teeth; generating, with the processor, a visual overlay identifying the error condition; outputting the visual overlay to a display of the augmented reality device, wherein the visual overlay is superimposed over a view of the patient's teeth and of the appliance placed on the patient's teeth.

The error condition may include a gap between the appliance and its corresponding tooth; alternatively or additionally, the error condition may include deformation of the appliance beyond a deformation threshold. Outputting the visual overlay may comprise displaying the error condition in a color. Identifying the error condition may comprise determining, using an image of the orthodontic appliance, a region of poor fit between the patient's teeth and the orthodontic appliance. In any of these methods, the orthodontic appliance may comprise an aligner (e.g., a shell aligner). Any of these methods may include identifying the error condition by estimating forces acting on the patient's teeth and indicating on the visual overlay where the forces exceed a threshold value. For example, estimating forces acting on the patient's teeth may comprise identifying one or more elastics attached to the dental appliance.

In any of the methods described herein, outputting the visual overlay to a display of the augmented reality device may comprise outputting the visual overlay to a display device worn on or over the user's head.

Also described herein are systems configured to perform any of the methods described herein, including a system comprising: an augmented reality display; one or more processors; and a memory coupled to the one or more processors, the memory configured to store computer-program instructions, that, when executed by the one or more processors, perform a computer-implemented method comprising: capturing, with a processor of an augmented reality device, image data of a patient's teeth and of an aligner placed on the patient's teeth; identifying from the image data, with the processor, an error condition indicative of improper aligner fit on the patient's teeth; generating, with the processor, a visual overlay identifying the error condition; outputting the visual overlay to a display of the augmented reality device, wherein the visual overlay is superimposed over a view of the patient's teeth and of the aligner placed on the patient's teeth.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4B is an example of a superposition (e.g., overlay) view of an AR system output showing deviation of a patient's teeth from a treatment plan.

FIG. 4C is a schematic (e.g., flowchart) showing an example of a method of evaluating an orthodontic treatment.

DETAILED DESCRIPTION

Figure 1A:
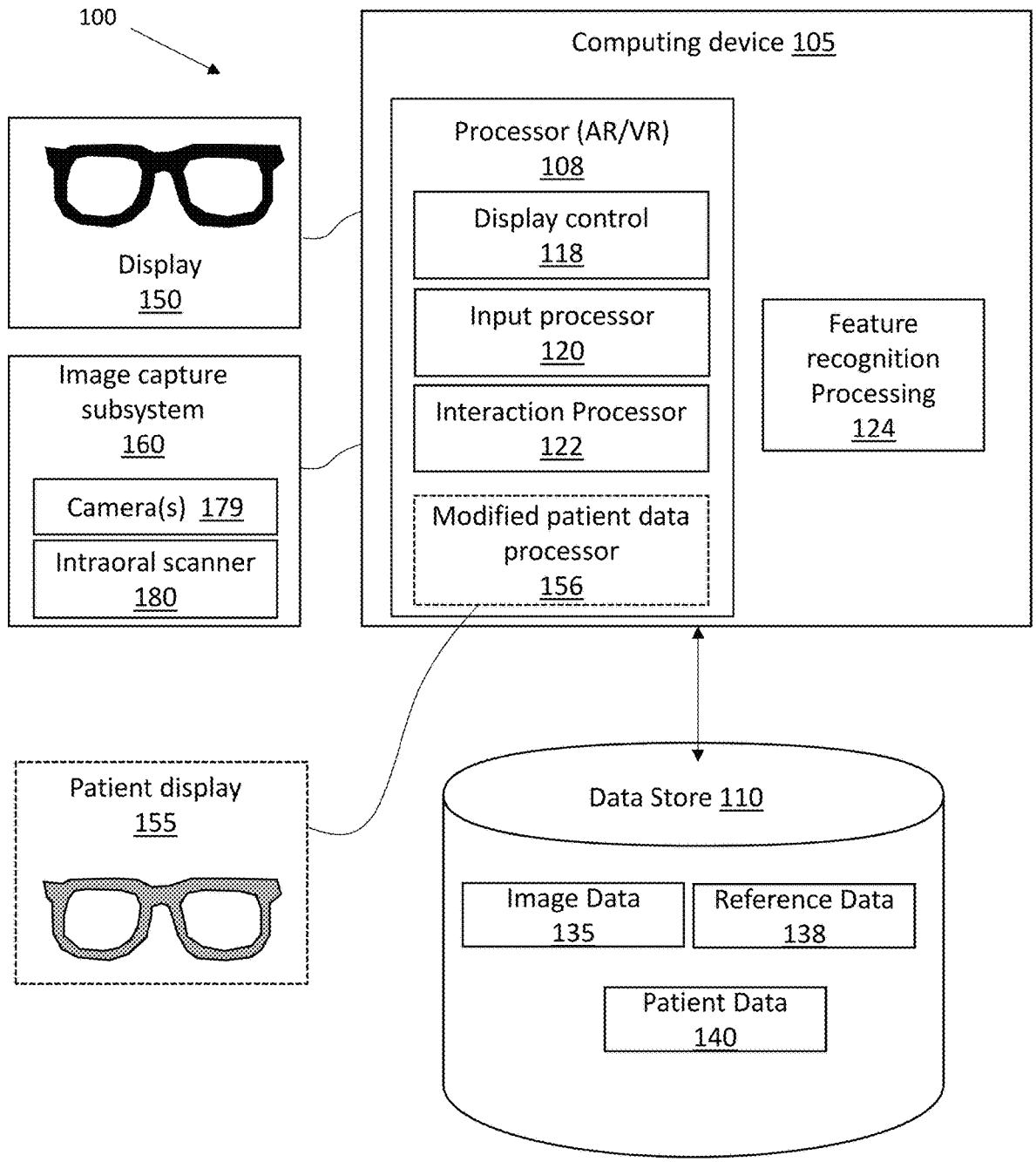
FIG. 1A illustrates one embodiment of an AR system for providing augmented reality enhancements to a dental practitioner.

Described herein are methods and apparatuses for providing augmented reality (AR) and/or virtual reality (VR) enhancements to dentists, orthodontists, dental hygienists, or other dental practitioners. An AR apparatus (e.g., an AR system, also referred to herein as an AR device) may provide real-time information to a dental practitioner based on an analysis of the mouth and/or dental arch of a patient as viewed through an AR display.

For example, the AR system may provide information about a dental arch based on images captured of the patient by the AR system. The AR system may also provide additional information based on a comparison of images captured by the AR system and previous data recorded for the patient. For example, previous images, scans, models, clinical data or other patient history may be compared to the images captured by the AR system, and a result of the comparison may be provided to the dental practitioner as a visual overlay on the real-world scene viewed by the dental practitioner through an AR display of the AR system. Previous data about the patient may also be provided in the visual overlay.

Additionally, image data from the AR system may be used to facilitate dental procedures such as drilling, grinding of a tooth, placement of an attachment on a tooth, placement of a bracket on a tooth (e.g., a bracket placed in the middle of the crown of a tooth), placement of other objects in pre-defined or automatically identified positions, intraoral scanning, and so on. The AR system may update information provided to a dental practitioner or provide feedback to the dental practitioner in real time or near real time during the course of the dental practitioner interacting with the patient.

As described herein, an AR system may provide information to the dental practitioner based on analysis of image data. For example, the AR system may analyze an image or stream of images of a patient's oral cavity and dental arch and determine an area of interest present in the image data. The AR system may determine if one or more teeth in an image indicate excessive wear, plaque, deposits, cracks, cavities, or other characteristics of interest to dental practitioners. The areas of interest may be determined based on processing an image of a dental arch or tooth taken by the AR system using one or more dental condition profiles in a data store. In some embodiments, the AR system may analyze an image of a tooth, multiple teeth, or a dental arch using dental condition profiles generated using machine learning techniques and training data of previous images of teeth. Examples of machine learning techniques (including in particular, deep learning for use with dental applications) may be found, for example, in U.S. provisional patent application No. 62/582,785, titled "DEEP LEARNING FOR TOOTH DETECTION AND EVALUATION," filed on Nov. 7, 2017, and any utility application claiming priority thereto, herein incorporated by reference in its entirety.

After the AR system determines one or more areas of interest, the AR display may then display real world data to a dental practitioner along with a visual overlay highlighting the areas of interest to the dental practitioner. In an example, the AR display may include lenses through which a wearer views the physical world, and the visual overlay may be projected onto the lenses. Alternatively, the visual overlay may be projected directly onto a wearer's eyes. For example, a tooth may be highlighted in a different color, circled, or otherwise indicated as having a characteristic in a visual overlay displayed by the AR system. For example, the AR system may provide different indicators for different characteristics or dental conditions. Furthermore, an area of interest may be highlighted, and a reason for the area of interest may be output in another portion of the display of the AR system or may be output in another manner, such as audio. Additionally, the AR system may also enhance a live view of the patient, such as by providing light enhancements that improve viewing of the patient or providing a zoomed in image of a portion of a patient's mouth.

As described herein, the AR system may provide information to the dental practitioner based on analysis of the patient and/or in view of previous patient data. For example, the AR system may compare images or models from a previous visit to current images of the patient's dental arch. The AR system may then determine one or more areas of interest based on the comparison. For example, the AR system may identify changes since a last scan, analysis of wear over time, feedback on orthodontic treatment, or other analysis of changes. The AR system may then mark the changes on a display of the AR system. The AR system may also superimpose previous patient data on a display. For example, the AR system may show a previous scan or previous dental arch superimposed onto a display.

Additionally, the AR system may provide interactive feedback or other updated information to the dental practitioner based on an interaction with the patient. For example, the feedback may be provided during an intra-oral treatment such as a dental procedure. The AR system may output to a display of the AR system recommended steps to take during an implant procedure, drilling procedure, grinding procedure, etc. For example, the AR system may show where to remove material for an insertion path, potential undercuts of neighboring teeth, placement of a hole for an implant, drilling depth, drilling direction, or the like. Similarly, the AR system may provide an indication of material to remove during interproximal reduction. The AR system may also provide feedback regarding placement of an attachment on a tooth. The AR system may also superimpose an occlusion map onto the patient's teeth in a display of the AR system. The AR system may also update a superimposed occlusion map if it changes while a dental practitioner is performing a dental procedure. An AR system may also provide feedback based on other information or analysis performed on images or other data received about a patient.

As further described herein, the AR system may allow a user to virtually select and manipulate one or more of a patient's teeth, and to change or provide treatment planning for the patient. The AR system can produce a visual overlay that shows the virtual manipulation, and how it will affect the treatment result. For example, a user can move or rotate one or more virtual teeth of the patient, and if satisfied with the placement, can implement the manipulation into the treatment planning.

Additionally, the AR system can identify error conditions with a patient's dental appliance, such as poor fit or misalignment of the dental appliance on the patient's teeth. The AR system can provide an overlay identifying the error conditions, which can be used to further fine tune the fitment of dental appliances.

The methods and apparatus described herein provide significant advantages over traditional techniques for dentistry and orthodontics, and can improve every aspect of a dental practice. Dental hygienists can use an AR system as described herein to better interact with a patient and identify potential dental issues that a dental hygienist is qualified to address, such as gum swelling or plaque caused by poor dental hygiene. The AR system may automatically process image data from the image capture subsystem to identify, for example, tooth wear, gum swelling, gum discoloration, plaque, etc. and call these dental conditions to the attention of the dental hygienist.

Similarly, a dentist may use an AR system that provides real-time feedback as described herein to improve his or her accuracy in performing intraoral procedures such as drilling a tooth, grinding a tooth, placing an attachment on a tooth, placing an implant, and so on. The AR system also presents information to a dental practitioner while the dental practitioner views a patient, and may reduce or eliminate a need for the dental practitioner to look away from the patient to a computer screen or chart. Additionally, an orthodontist may use an AR system as described herein to improve his analysis of how an orthodontic treatment plan is progressing, to improve performance of intraoral procedures, and so on. Embodiments therefore improve the efficiency of interfacing with patients, the accuracy of dental procedures and the identification of dental conditions. For example, embodiments enable a dental practitioner to work while looking exclusively at the patient's jaws, without any reason to turn his or her head toward a screen or monitor (e.g., of a computing device for an intraoral scanner).

As described herein, an intraoral scanner may use an AR display as a primary or secondary display for controlling an intraoral scanning procedure. The AR display may be worn by a dental practitioner that uses the intraoral scanner to image a patient's dental arch and generate a virtual three-dimensional model of that dental arch. The AR display may provide a two-dimensional (2-D) or three-dimensional (3-D) menu of options for controlling the intraoral scan procedure. Additionally, the AR display may be used to provide a zoomed in view of a region of the dental arch being scanned. Additionally, the AR display may be used to provide a virtual overlay of a virtual 3-D model of the dental arch based on images generated by the intraoral scanner during an intraoral scan procedure.

During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The intraoral scanner can automatically generate a 3D model of the patient's teeth, which can be used for treatment planning.

As further described herein, an image capture subsystem of an AR display may be used to generate multiple images of a patient's teeth. The image capture subsystem may generate a stream of images, and processing logic may analyze the stream of images to select a subset of those images. The selected subset of images may then be saved and used to generate a model associated with a dental arch or jaw, such as an articulation model of the patient's jaw. Additionally, a dental practitioner wearing the AR display may generate voice notes and append those voice notes to images taken by the image capture subsystem of the AR display.

As described herein, an AR system is a device that enables a live direct or indirect view of a physical, real-world environment and that augments the view of the physical real-world environment by computer generated sensory input such as sound, video, or graphics. An AR system may include an AR display that includes glasses or other lenses that have one or more cameras attached to capture images of a patient. The AR display may also have a projector that projects images onto the glasses or lenses to provide a visual overlay to a dental practitioner. The visual overlay can be superimposed over the real world image that the dental practitioner sees through the glasses or lenses. The AR display can be worn by a dental practitioner, and can include AR glasses, AR goggles, or an AR headset. While some embodiments described herein are discussed with reference to a worn AR display, it should be understood that the AR system can use other types of displays.

Additionally, it should be understood that reference to an AR system also apply to a virtual reality (VR) system. A VR system is similar to an AR system, except that an AR system allows a wearer or viewer to see an augmented version of the real world, while a VR system provides a purely simulated environment. A VR system artificially creates sensory experiences that can include sight, touch, sound, and/or other senses, and presents these sensory experiences onto a VR display. Any reference made herein to any type of AR system and/or AR display applies equally to a VR system and/or VR display.

FIG. 1A illustrates one embodiment of an AR system 100 for providing augmented reality enhancements to a dental practitioner. The AR system 100 includes a computing device 105, an AR display 150, a patient display 155, an image capture subsystem 160, and a data store 110. In some embodiments, the image capture subsystem 160 is a component of the AR display 150. In some embodiments, multiple components shown in FIG. 1A may be integrated into a device that houses the AR display 150. For example, the computing device 105 and image capture subsystem 160 may be integrated into glasses or a headset to be worn by a dental practitioner. In some embodiments, the computing device 105 may be separate from the AR display 150, but connected through either a wired or wireless connection to a processing device in the AR display 150. Additionally, the data store 110 may be attached to the AR display 150, may be directly connected to computing device 105, and/or may be accessed by computing device 105 over a network (not shown). In some embodiments, the computing device 105 and data store 110 may be collocated and accessed by the AR display 150 over a network.

Computing device 105 may include a processor, memory, secondary storage, one or more input devices (e.g., such as a keyboard, mouse, tablet, speakers, or the like), one or more output devices (e.g., a display, a printer, etc.), and/or other hardware components. Computing device 105 may be connected to data store 110 either directly or via a network. The network may be a local area network (LAN), a public wide area network (WAN) (e.g., the Internet), a private WAN (e.g., an intranet), or a combination thereof. The computing device 105 may be integrated into the AR display 150 or image capture subsystem 160 in some embodiments to improve mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

Figure 1B:
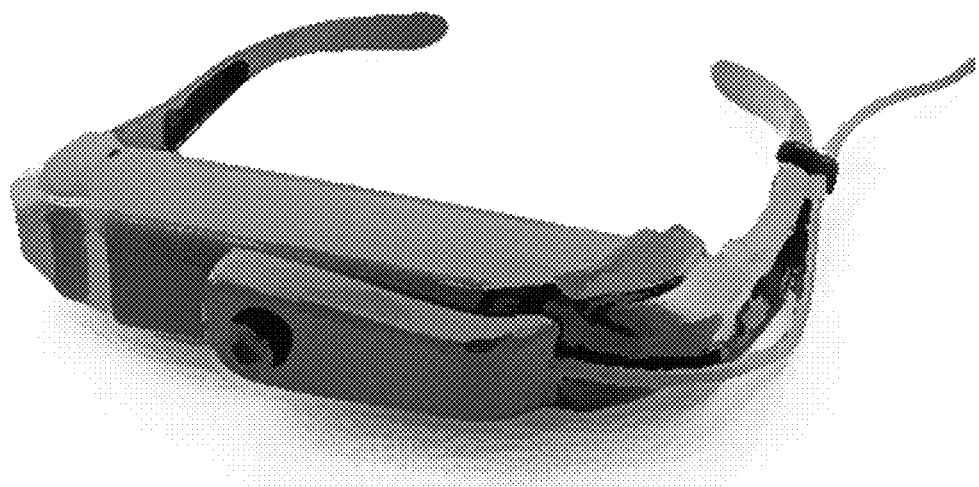
FIGS. 1B-1E show variations of an AR and VR displays, according to the present disclosure.
Figure 1C:
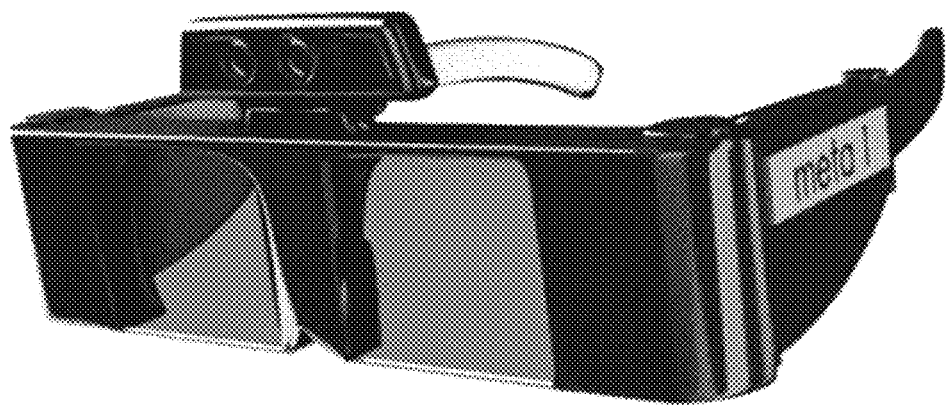
Figure 1D:
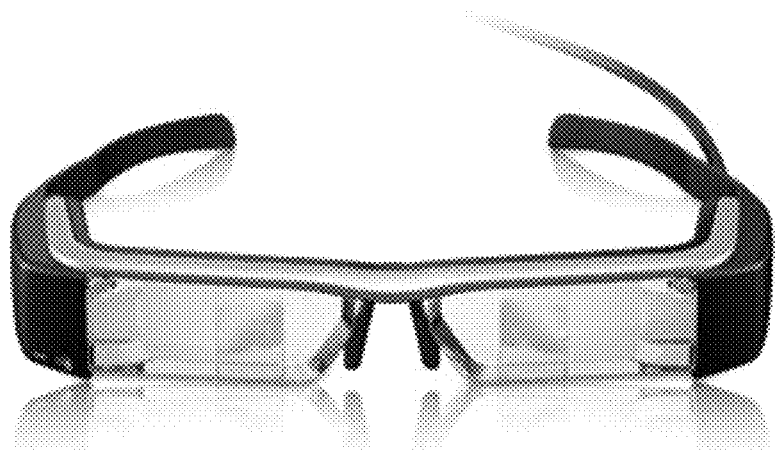
Figure 1E:
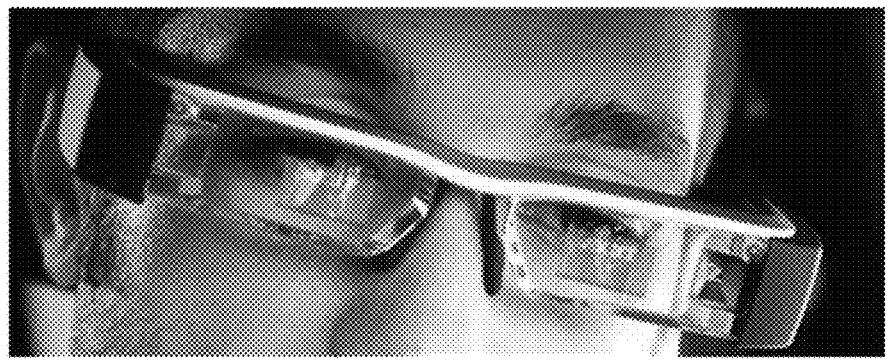

The AR display 150 may include lenses through which a wearer (e.g., a dental practitioner) may see a physical, real-world environment (e.g., a patient's oral cavity) and a projector for projecting visual elements onto the lenses. Examples of AR displays include HoloLens®, Google Glass®, Vuzix Smart Glasses®, and Sony SmartEyeGlass®. Examples of AR displays are shown in FIGS. 1C-1E. The AR display 150 may therefore overlay information for a dental practitioner onto the lenses in a position in the field of view of the practitioner that corresponds to a location of an identified area of interest. To determine where to display information, the AR display 150 may include one or more sensors to track the eyes of a user and/or determine a position of the user in relation to positions of objects viewed by the user. The AR display 150 may also use images provided from image capture subsystem 160 to determine where to display information to the dental practitioner. In some embodiments, the image capture subsystem 160 is mounted to the AR display 150.

The patient display 155 may be similar to the AR display 150 as described above, or alternatively, may be a VR or head-mounted display in which the patient cannot see the physical, real-world environment. An example of a VR display is shown in FIG. 1B. The patient display may have one or two small displays, with lenses and semi-transparent mirrors embedded in eyeglasses, a visor, or a helmet. The display(s) may include cathode ray tubes (CRT), liquid crystal displays (LCDs), liquid crystal on silicon (LCos), or organic light-emitting diodes (OLED). The image data from the image capture subsystem 160 and/or the visual overlay generated based on the image data may be output to the patient display 155. This may enable the patient to view dental conditions of his teeth or gums that a dental practitioner is seeing (and possibly describing). This may facilitate an explanation of the dental conditions to the patient by the dental practitioner. Image data from the image capture subsystem and/or visual overlays may also be sent to the VR display, for example, during dental procedures.

The image capture subsystem can include one or more camera(s) 179. The camera(s) may comprise high definition cameras to accurately capture the structure of areas of interest of a patient. In some embodiments, the camera(s) may include one or more cameras that capture a wide field of view and additional cameras for capturing a narrow field of view (e.g., for a region identified as containing an area of interest). In some embodiments, the image capture subsystem 160 may include additional cameras to provide additional streams of image data. Additional cameras may be used to improve three dimensional image quality.

In some embodiments, the image capture subsystem 160 may include one or more light sources to illuminate a patient for capturing images. Such light sources may include infrared, ultraviolet, or other wavelength light sources (e.g., LEDs or the like). These light sources may illuminate an oral cavity to provide additional data over information available from the visible light spectrum. For example, certain wavelengths such as infrared or ultraviolet wavelengths may more clearly show certain dental conditions such as plaque or cavities. In addition, in some embodiments, light sources may provide structured light to enhance three-dimensional mapping of image data received from image capture subsystem 160. For example, the light sources may project lines or a grid onto viewed objects to provide additional information about depth to the computing device 105.

As a dental practitioner wearing the AR display 150 views a patient, the camera(s) 179 of image capture subsystem 160 may generate a stream of images that show the patient from the dental practitioner's point of view. The images may also be displayed on the patient display 155. The camera(s) may be or include a charge-coupled device (CCD) sensor and/or a complementary metal-oxide semiconductor (CMOS) sensor. The image capture subsystem 160 may provide images or video to the computing device 105 for processing. For example, the image capture subsystem 160 may provide images to the computing device 105 that the computing device analyzes to determine areas of interest on a dental arch or otherwise in an oral cavity viewed by a dental practitioner. The image capture subsystem 160 may also provide images to the computing device 105 or AR display 150 that are used to coordinate the position of elements of a visual overlay to display on AR display 150 so that the visual overlay is superimposed over the real-world environment viewed by the dental practitioner. In some embodiments, the images captured by the camera(s) may be stored in data store 110. For example, the image data 135 may be stored in data store 110 as a record of patient history or for computing device 105 to use for analysis of the patient. The image capture subsystem 160 may transmit the discrete images or video to the computing device 105. Computing device 105 may store the image data 135 in data store 110.

In some embodiments, the image capture subsystem 160 provides two-dimensional data. In some embodiments, the image capture subsystem 160 may provide three-dimensional data or stereoscopic image data that may be processed to produce three-dimensional data. For example, the image capture subsystem 160 may have two cameras with a known separation and known imaging angles that simultaneously capture image data. The stereoscopic image data may be provided to computing device 105 as a single stream of image data or as two separate streams of image data. The stereoscopic image data may be used to provide an estimation of depth for objects viewed through the AR display 150. For example, the computing device 105 may use the stereoscopic image data to identify a three dimensional location of a tooth in the field of view of the image capture subsystem 160.

The image capture subsystem 160 can further include an intraoral scanner 180. In one embodiment, the intraoral scanner 180 includes an image sensor, a communication module and one or more inputs (e.g., buttons, a touch sensor, switches, sliders, etc.). The image sensor generates intraoral images of a patient and the communication module transmits those intraoral images to computing device 105. The computing device may then display the intraoral images or a representation of the dental arch of the patient generated from the intraoral images (e.g., a virtual 3D model of a dental site of the patient) via a visual overlay sent to the AR display 150 or patient display 155. A user may then use the one or more inputs from the intraoral scanner, motion gestures, or other inputs to manipulate the intraoral images or the representation (e.g., virtual 3-D model) generated from the intraoral images. The intraoral images or virtual 3-D model may be shown in the AR display as they are manipulated.

Intraoral scanner 180 may include a probe (e.g., a hand held probe) for optically capturing three dimensional structures (e.g., by confocal focusing of an array of light beams). Intraoral scanner 180 may also include other components such as optical components, an accelerometer, communication components, a gyroscope, processing devices, and so on. One example of an intraoral scanner 180 is the iTero® intraoral digital scanner manufactured by Align Technology, Inc.

The intraoral scanner 180 may be used to perform an intraoral scan of a patient's oral cavity. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the intraoral scanner 180 at a first position in the oral cavity, move the intraoral scanner 180 within the oral cavity to a second position while the video is being taken, and then stop recording the video. The intraoral scanner 180 may transmit the discrete intraoral images or intraoral video to the computing device 105. Computing device 105 may store and/or process the discrete intraoral images or intraoral video in data store 110.

Once an intraoral scan is complete, the processor can use the intraoral scan data from the one or more scans of the various segments to generate a virtual 3D model of a scanned dental site. The dental practitioner can view the scans in detail at various angles by rotating, moving, zooming in or out, etc. of the virtual 3D model. The dental practitioner may make a determination whether the quality of the scans are adequate, or whether particular segments or portions of segments should be rescanned. The dental practitioner may also navigate back to the scan mode to perform additional scans. Once the scans are complete, the scans and/or virtual 3D model can be stored in data store 110 as reference data 138.

The computing device 105 may include AR processor 108. The AR processor 108 may analyze image data 135 from a data store 110 or directly from an image capture subsystem 160. The AR processor 108 may then identify areas of interest to present in a visual overlay on AR display 150 and/or generate additional information to present on the AR display 150. The information provided on an AR display 150 may depend on a procedure to be performed, a wearer of the AR display 150, information known about a patient, and so on. For example, during a routine checkup, the computing device 105 may provide patient history to a dental practitioner and/or display areas of interest identified based on image data 135.

In one embodiment, AR processor 108 includes a display control 118, an input processor 120, an interaction processor 122, and a modified patient data processor 156.

Display control 118 is responsible for determining how to present and/or call out the identified areas of interest on the AR display 150. AR display control 118 may provide indications or indicators highlighting identified AOIs. The AR display control 118 may determine a position to project a virtual object in a visual overlay on an AR display 150 such that the overlay is positioned in the line of sight of the dental practitioner over the AOI. The virtual object may include text, numbers, a contour, colors, graphical images and/or other virtual objects. For instance, the AR display control 118 may determine from the position of the AOI in the image data 135 a corresponding position to project an indicator or indication on the AR display 150. As an example, the AR display control may provide an indication of wear on a tooth by highlighting the worn area on the tooth in a notable color (e.g., that contrasts with a background on which the indication is superimposed) and/or or by providing an indicator pointing to the tooth. In some embodiments, the AR display 150 may provide additional indicators separate from a position corresponding to the AOI in order to provide additional data to a dental practitioner.

The AR display control 118 may provide the indications in the form of flags, markings, contours, text, images, and/or sounds (e.g., in the form of speech). In some embodiments, the AR display module 118 may provide a contour (e.g., via contour fitting) so as to follow a tooth contour or gingival contour in the image data 135. As an illustration, a contour corresponding to a tooth wear diagnostic assistance indication may be placed so as to follow a contour of the worn tooth. A contour may also follow a previous contour of the tooth or other dental feature. For example, a visual overlay may include a contour showing a previous shape of a tooth, or a difference between a previous shape of a tooth and a current shape of the tooth. Such a contour may be placed in the visual overlay so as to be superimposed over the real-world view of the tooth in question or adjacent (e.g., touching) the tooth in question. As an illustration, a contour corresponding to a previous or future position of a tooth may be displayed so as to follow the projected path of the tooth portion which is missing, or a contour corresponding to missing gingival scan data may be placed so as to follow the projected path of the gingival portion which is missing.

Input processor 120 handles all inputs from the display 150 or patient display 155. For example, the input processor 120 may identify virtual selections by a user that are captured by the camera(s) of the image capture subsystem. The virtual selections may be, for example, a hand gesture of the user that identifies the virtual selection, such as by virtually tapping, touching, or selecting one or more of the patient's teeth. The input processor 120 can access data store 110 to use image data 135, reference data 138, and patient data 140 while compiling the virtual selections.

Interaction processor 122 processes virtual manipulations of the virtual selections described above. For example, a user can virtually manipulate the virtual selections with hand gestures by virtually moving, expanding, or rotating the virtual selection to a new position or orientation. The interaction processor 122 identifies these virtual manipulations and applies the manipulation to image data 135, reference data 138, and patient data 140, to determine a virtual overlay corresponding to the new position and orientation of the virtual selection.

Any of the apparatuses described herein may be configured to provide additional output to a patient or third party, in addition to the output provided to the dental professional (e.g., in addition to display 150 in FIG. 1A). This patient-specific output may be modified from the data and output shown to the dental professional. For example, this output may be modified to include less, different, or time-delayed versions of the output displayed to the primary user, the dental professional. Thus, any of these apparatuses may include a modified patient data processor 156 that is connected to the patient display 155. In some examples, the patient display is configured to simplify the output shown to the patient, compared to the primary user.

The computing device 105 can further include feature recognition processing 124, which is responsible for identifying areas of interest (AOIs) from image data 135 received from image capture subsystem 160. The image data may be images of a patient's oral cavity viewed by a dental practitioner wearing the AR display 150. The feature recognition processing 124 may also identify AOIs from reference data 138, which may include patient history, virtual 3D models generated from intraoral scan data, or other patient data. Such areas of interest may include areas indicative of tooth wear, areas indicative of tooth decay, areas indicative of receding gums, a gum line, a patient bite, a margin line (e.g., margin line of one or more preparation teeth), and so forth. Areas of interest may also include areas indicative of foreign objects (e.g., studs, bridges, etc.), areas for the dental practitioner to perform planned treatment, or the like. Furthermore, feature recognition processing 124 may identify error conditions with a dental appliance on the patient's teeth, such as poor fit, poor attachment, etc. The feature recognition processing 124 may, in identifying an AOI, analyze patient image data 135. The analysis may involve direct analysis (e.g., pixel-based and/or other point-based analysis), the application of machine learning, the application of image registration, and/or the application of image recognition. The feature recognition processing 124 may identify areas of interest directly from the image data 135 received from the image capture subsystem 160 or based on a comparison of the received image data 135 and reference data 138, or previous patient data 140. For example, the feature recognition processing 124 may use one or more algorithms or detection rules to analyze the shape of a tooth, color of a tooth, position of a tooth, or other characteristics of a tooth to determine if there is any AOI that should be highlighted for a dental practitioner. Examples of machine learning techniques (including in particular, deep learning for use with dental applications) may be found, for example, in U.S. provisional patent application No. 62/582,785, titled "DEEP LEARNING FOR TOOTH DETECTION AND EVALUATION," filed on Nov. 7, 2017, herein incorporated by reference in its entirety.

Figure 2:
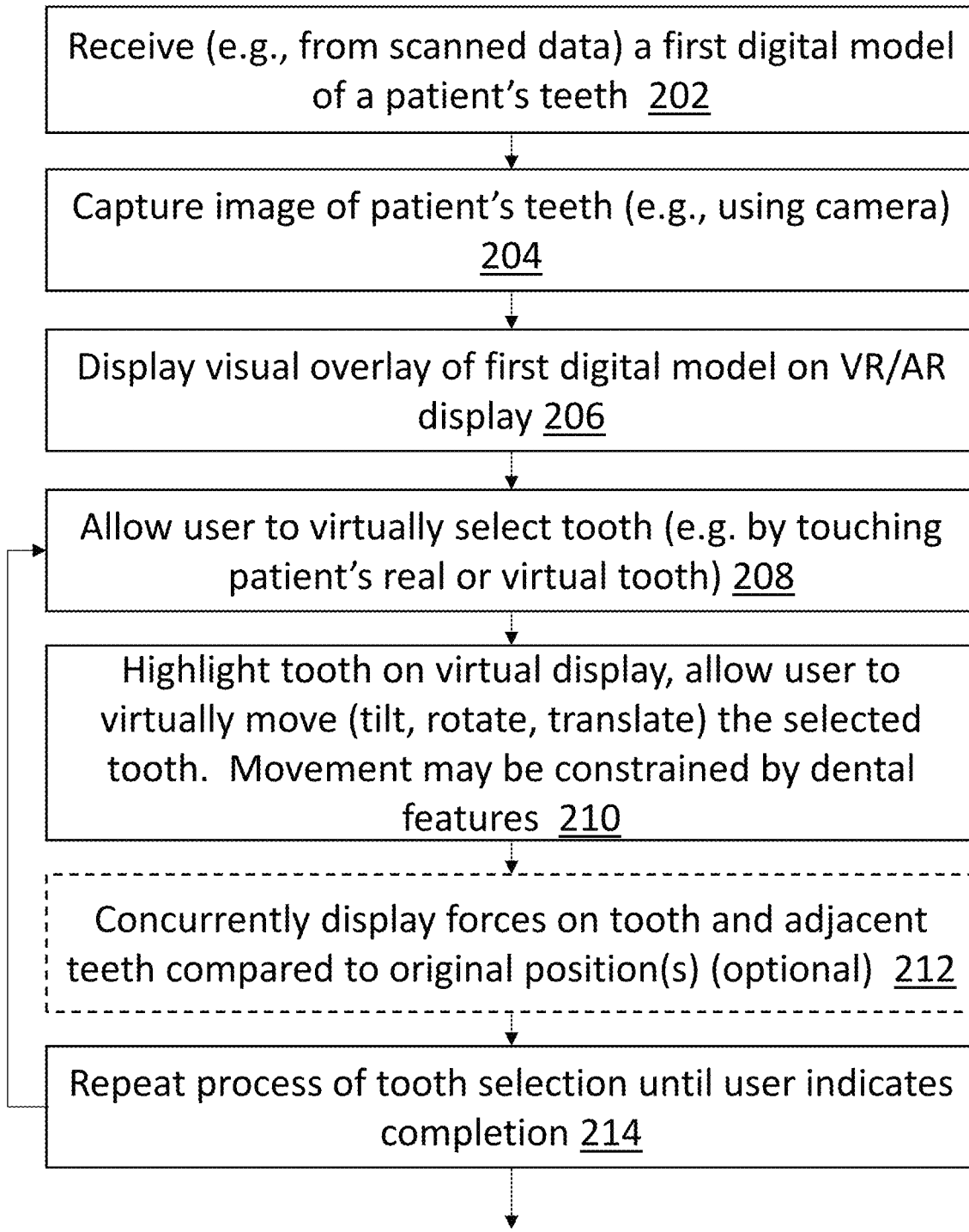
FIG. 2 is a flowchart describing the use of an AR system to develop a treatment plan for an orthodontic patient.

FIG. 2 is a flowchart describing the use of an AR system to develop a treatment plan for an orthodontic patient. At step 202 of the flowchart, the AR system can receive a first digital model of a patient's teeth representing a dental arch. For example, referring to FIG. 1A, processor 108 can receive scans and/or virtual 3D models of the patient's teeth from reference data 138 of data store 110.

At step 204 of the flowchart, the AR system can capture one or more images of the patient's teeth. Referring again to FIG. 1A, camera(s) 179 of the image capture subsystem 160 can capture 2D or 3D images of the patient's teeth. These images can be stored in data store 110 as image data 135.

In some examples, according to step 206 of the flowchart, the first digital model from step 202 can be displayed as a visual overlay onto an AR display of the AR system. A user of the AR display, such as a physician, can view the patient's teeth in real-time along with the visual overlay of the first virtual model over the patient's teeth. Referring to FIG. 1A, display control 118 of the processor 108 can generate the visual overlay from the reference data 138 and display the visual overlay onto the AR display 150.

Next, at step 208 of the flowchart, the AR system allows a user to virtually interact with the patient's teeth. The user can virtually select one or more teeth, or alternatively, add a virtual attachment to one or more of the patient's teeth. The virtual selection can be, for example, physical or virtual touching of the patient's teeth. The virtual selection can be identified by the AR system by evaluating the movement of the user's hand in front of the camera(s) and identifying the position and orientation of the user's hand with respect to the real or first virtual model of the patient's teeth. Referring to FIG. 1A, the input processor 120 and/or interaction processor 122 of the processor 108 compute and process the virtual selection from the user's gestures, the image data 135, and reference data 138.

At step 210 of the flowchart, the AR system can highlight the virtual selection on the AR display by generating a visual overlay identifying the virtual selection. The visual overlay identifying the selection can be, for example, and outline of the selection, or visual shading or colorizing of the selected one or more teeth.

Still at step 210, the user can virtually manipulate the virtual selection, such as by moving, tilting, rotating, or translating the virtual selection. For example, the physician can select one or more teeth (again captured by the camera(s) of the AR system), and can virtually move those teeth to a different position in the patient's jaw, or rotate the one or more teeth to be in a more optimal position. The first digital model of the patient's teeth can be updated in the system to reflect the virtual manipulation, and the visual overlay can be updated and displayed to correspond to the virtual manipulation. The movement of the virtual selection can optionally be constrained by dental features of the patient, such as the location of adjacent teeth, the size of the patient's jaw, the jaw or facial shape/structure of the patient, etc. Referring again to FIG. 1A, interaction processor 122 processes the virtual manipulation, and applies the virtual manipulation to the image data 135 and reference data 138 to provide an updated digital model.

At step 212 of the flowchart, the AR system can optionally display forces on the virtually manipulated teeth (and adjacent teeth) compared to the original positions. This can aid a physician in evaluating the effects of a particular manipulation. If the physician determines or sees that the forces acting on the manipulated teeth are too great, the physician may decide to cancel the manipulation or further adjust the position/orientation of the selected teeth.

According to step 214 of the flowchart, steps 208-212 can be repeated as desired by the user until the user indicates completion. Upon completion, the first digital model can be stored in reference data 138 of data store 110 as a second or modified digital model.

Figure 3:
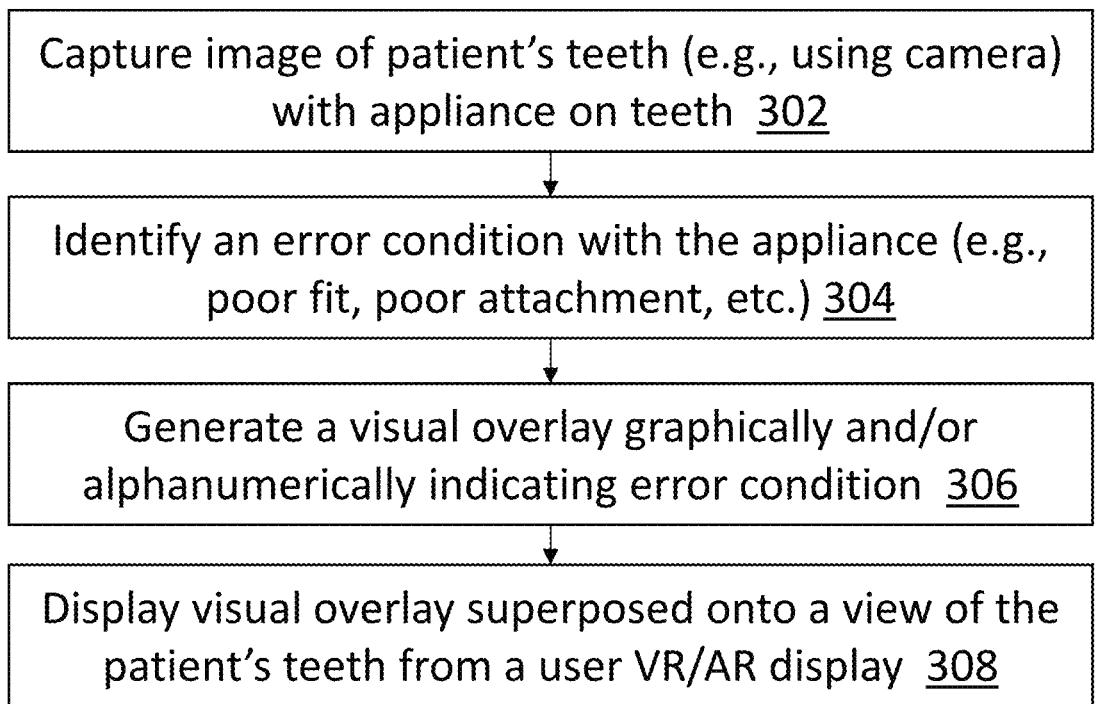
FIG. 3 is a flowchart describing the use of an AR system to evaluate fitment of an orthodontic appliance.

FIG. 3 is a flowchart describing the use of an AR system to evaluate fitment of an orthodontic appliance. At step 302 of the flowchart, the AR system can capture one or more images of the patient's teeth with a dental appliance placed on the teeth. Referring to FIG. 1A, camera(s) 179 of the image capture subsystem 160 can capture 2D or 3D images of the patient's teeth. These images can be stored in data store 110 as image data 135.

Next, at step 304 of the flowchart, the AR system can identify an error condition with the appliance from the images. The error condition can be, for example, improper appliance fit, poor attachment, etc. The error condition can be identified with the feature recognition processing 124 of FIG. 1A, which can identify gaps between the dental appliance and the teeth, bending/warping/deformation of the appliance beyond a threshold, etc.

At step 306 of the flowchart, the AR system can generate a visual overlay that graphically and/or alphanumerically indicates the error condition. The visual overlay can comprise outlines, shading, coloring, etc. Referring to FIG. 1A, display control 118 of the processor 108 can generate the visual overlay from the reference data 138 and image data 135.

At step 308 of the flowchart, the visual overlay from step 306 can be displayed onto an AR display of the AR system. A user of the AR display, such as a physician, can view the patient's teeth and dental appliance in real-time along with the visual overlay that graphically or alphanumerically indicates the error condition. Referring to FIG. 1A, display control 118 of the processor 108 can generate the visual overlay from the reference data 138 and image data 135 and display the visual overlay onto the AR display 150.

Figure 4A:
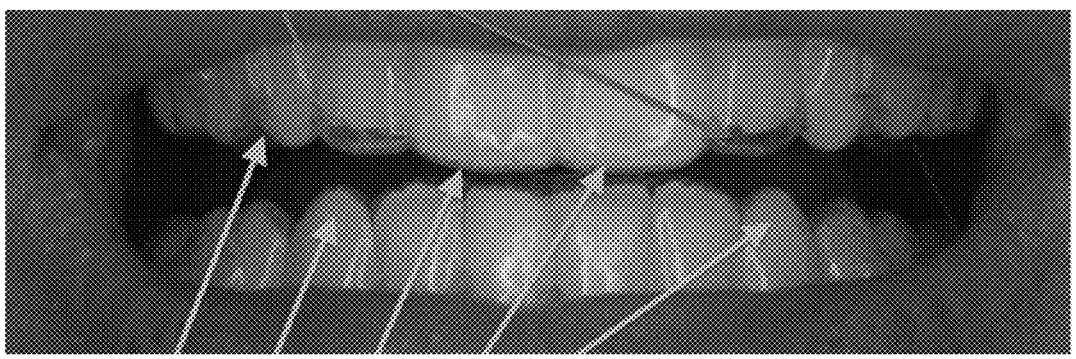
FIG. 4A illustrates examples of both good fit and poor fit in a dental appliance, and provides an example of what the error condition visual overlay of FIG. 3 may look like from the user's perspective.

FIG. 4A illustrates examples of both good fit and poor fit in a dental appliance, and provides an example of what the error condition visual overlay of FIG. 3 may look like from the user's perspective. Additionally, error conditions can be identified in the visual overlay with outlines or shading/color. For example, good/poor fit of an appliance may be identified by highlighting individual problem areas (e.g., red for poor fit, green for good fit). In another example, the visual overlay displays estimated forces acting on the patient's teeth where the forces exceed a threshold value (e.g., poor fit results in high forces acting on the patient's teeth, or an improperly placed band or attachment causes forces to exceed a threshold).

FIGS. 4B and 4C illustrate one example of a method of evaluating an orthodontic treatment (e.g., orthodontic treatment plan). As described in FIG. 4C, the method may be performed in and by an augmented reality apparatus; a physician may wear an AR display device, such as those described above. Initially, the apparatus may receive (e.g., in a processor) a first data set comprising a treatment plan for a patient's teeth 458. A treatment plan may include one or more (typically 4 or more, e.g., 5 or more, 6 or more, etc.) treatment stages, and may include information on the position and orientation (e.g., relative to the dental arch) of the patient's teeth at each step of the treatment plan. The apparatus may additionally or alternatively receive, from an augmented reality system worn by a dental practitioner, an image data set comprising a representation of the patient's current teeth 460. Alternatively or additionally, the apparatus may compare the first data set to the image data set to determine one or more variations from the treatment plan 462. Finally, the method or apparatus configured to perform the method may include displaying the one or more variations on a visual display of the augmented reality system worn by the dental practitioner superimposed over a view of the patient's teeth 464.

FIG. 4B illustrates one example of an overlay (e.g., superposition) display of a dental practitioner-worn AR display, showing deviation between the current position and/or orientation of the patient's teeth and the target position(s) and orientations of the patient's teeth at a later stage (e.g., stage 10, stage 11, stage 12, stage 13, stage 14, stage 15, stage 16, stage 17, etc.). In some variations the comparison may be made at each stage of the treatment plan and/or at the treatment plan having the lowest (e.g., numerically determined) deviation from the current teeth. FIG. 4B illustrates an example of an overlay configured to indicate one or more deviations from one of the treatment stages. In FIG. 4B, the marked region 488 indicates regions that have deviated (e.g., by an amount above a percent difference, e.g., 1%, 2%, 5%, 10%, 15%, 20%, 25%, 40%, 50%, etc.) from the augmented reality target (e.g., goal) of the percentage difference. Unmarked regions 487 show the current tooth positions/orientation.

Figure 5B:
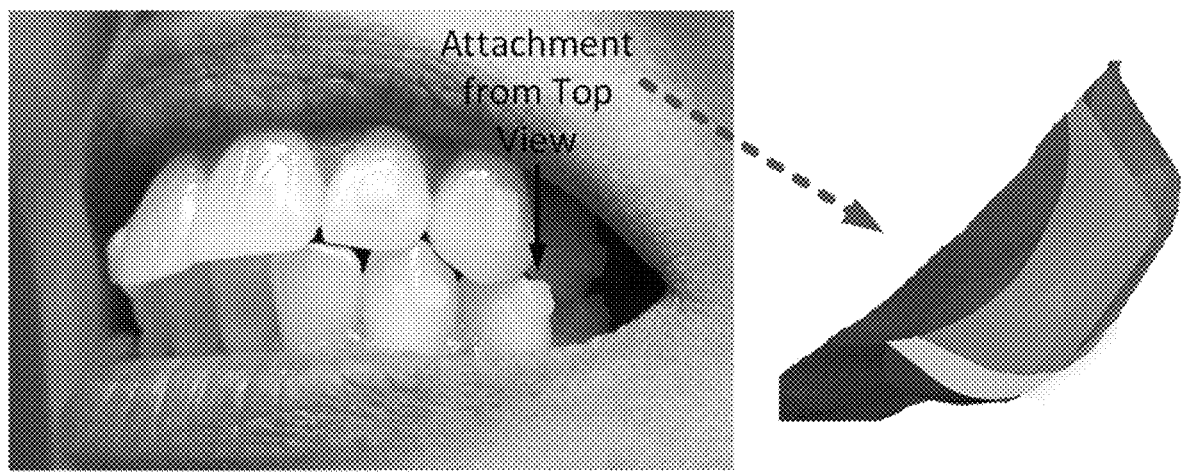
FIG. 5B is an example of a superposition view by an AR system showing mismatch of a planned attachment.
Figure 5A:
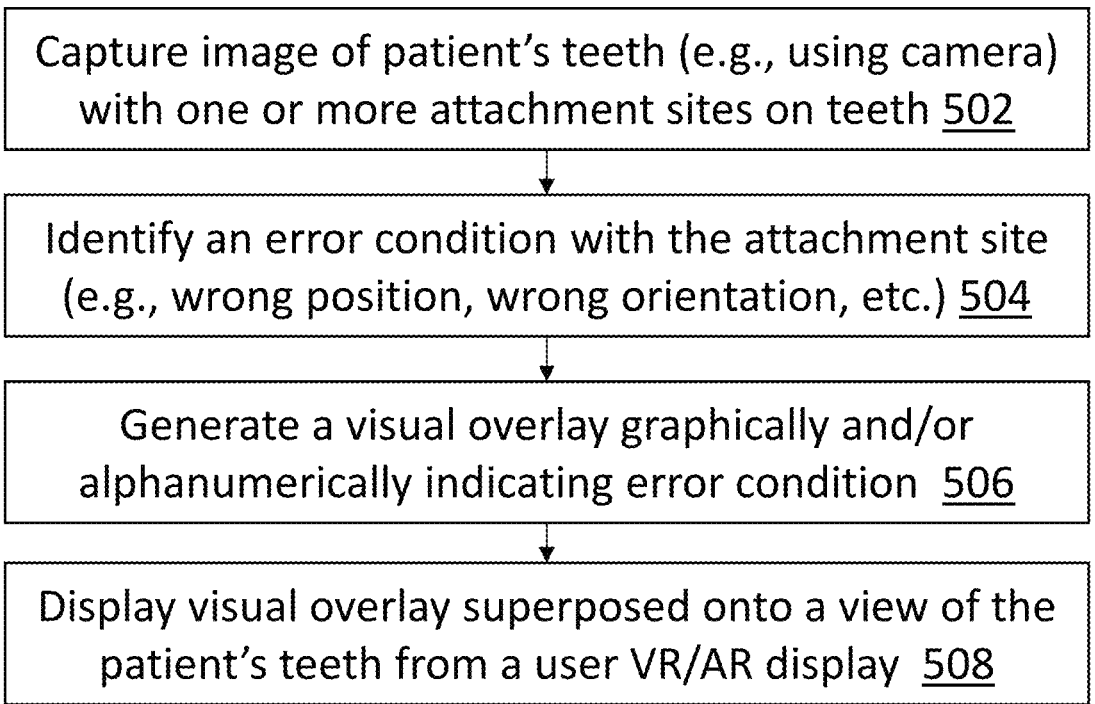
FIG. 5A is a flowchart describing the use of an AR system to evaluate attachments or potential attachments for an orthodontic appliance.

FIG. 5A is a flowchart describing the use of an AR system to evaluate attachments or potential attachments for an orthodontic appliance. At step 502 of the flowchart, the AR system can capture one or more images of the patient's teeth with one or more attachment sites on the teeth. Referring to FIG. 1A, camera(s) 179 of the image capture subsystem 160 can capture 2D or 3D images of the patient's teeth. These images can be stored in data store 110 as image data 135.

Next, at step 504 of the flowchart, the AR system can identify an error condition with the attachment from the images. The error condition can be, for example, an attachment location that differs from a target location, an attachment orientation that differs from a target orientation, improper forces, etc. The error condition can be identified with the feature recognition processing 124 of FIG. 1A, which can evaluate the attachment sites and process the forces applied by the attachment sites to the adjacent teeth to evaluate the effect of applying attachments to the attachment sites.

At step 506 of the flowchart, the AR system can generate a visual overlay that graphically and/or alphanumerically indicates the error condition. The visual overlay can comprise outlines, shading, coloring, force vectors, etc. Referring to FIG. 1A, display control 118 of the processor 108 can generate the visual overlay from the reference data 138 and image data 135.

At step 508 of the flowchart, the visual overlay from step 506 can be displayed onto an AR display of the AR system. A user of the AR display, such as a physician, can view the patient's teeth and attachment sites along with the visual overlay that graphically or alphanumerically indicates the error condition. Referring to FIG. 1A, display control 118 of the processor 108 can generate the visual overlay from the reference data 138 and image data 135 and display the visual overlay onto the AR display 150.

FIG. 5B shows an example of a superposition view by an AR system showing mismatch of a planned attachment position versus a formed attachment. In FIG. 5B (left) the patient's dentition (upper and lower arch) may be visible through the AR system and a virtual image of on attachment (FIG. 5B, right) may be displayed in an overlay atop the view of the dentition. In some variations, the user may rotate or manipulate the virtual image using a tool and/or hand gestures.

Figure 6:
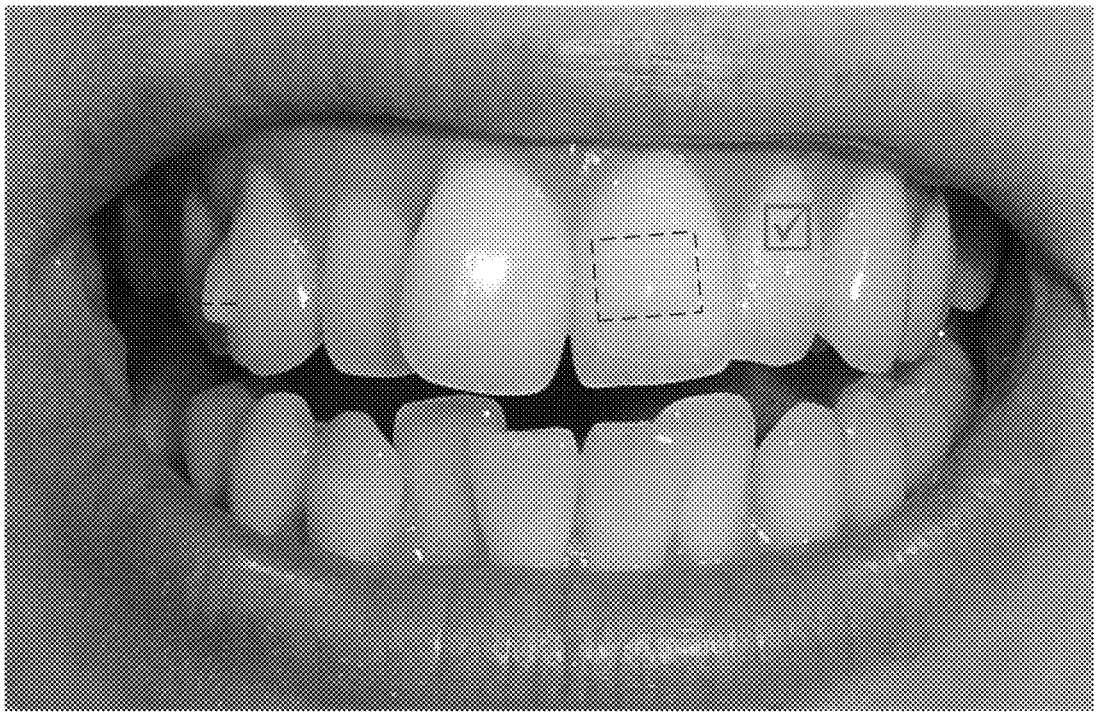
FIG. 6 illustrates examples of what the error condition visual overlay of FIG. 5A may look like from the user's perspective.

FIG. 6 illustrates examples of what the error condition visual overlay of FIG. 5A may look like from the user's perspective. For example, a good potential attachment site may be indicated with a visual marker, outline, or color to indicate its suitability for an attachment point (e.g., green box, check mark, etc.). Similarly, a poor potential attachment site may also be indicated with a visual marker, outline, or color to indicate that it is not a good location for an attachment (e.g., red box, X, etc.). Additionally, the visual overlay can indicate forces applied by a potential attachment site to adjacent teeth, such as with visual force vectors or alphanumeric data indicating the forces (and whether they surpass a force threshold).

Figure 11:
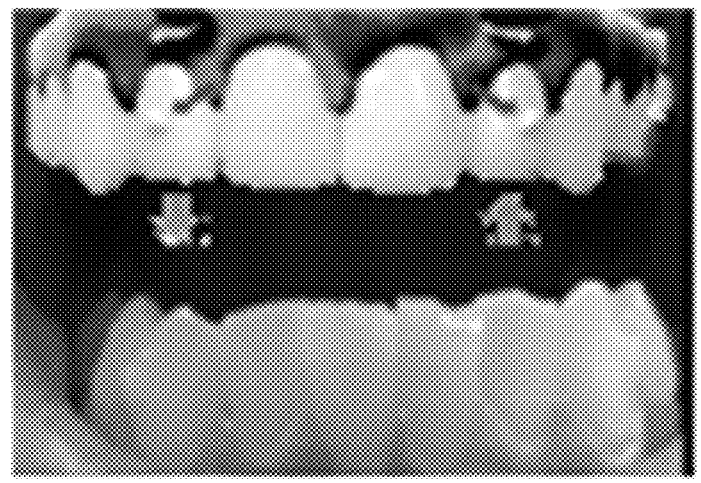
FIG. 11 is an example of an augmented reality (AR) view similar to that seen by a user (e.g., dental professional) operating one of the systems described herein, configured to show force(s) acting on the one or more teeth as a symbol, marking or alphanumeric code.

FIG. 11 illustrates one example of measuring and analyzing forces (including torques) operating on a patient's teeth when wearing an aligner and/or by superimposing the force vector representation onto the current tooth view observed by the dental professional. In FIG. 11, the image shows superimposing force and torques on the patient teeth by AR system.

Figure 7:
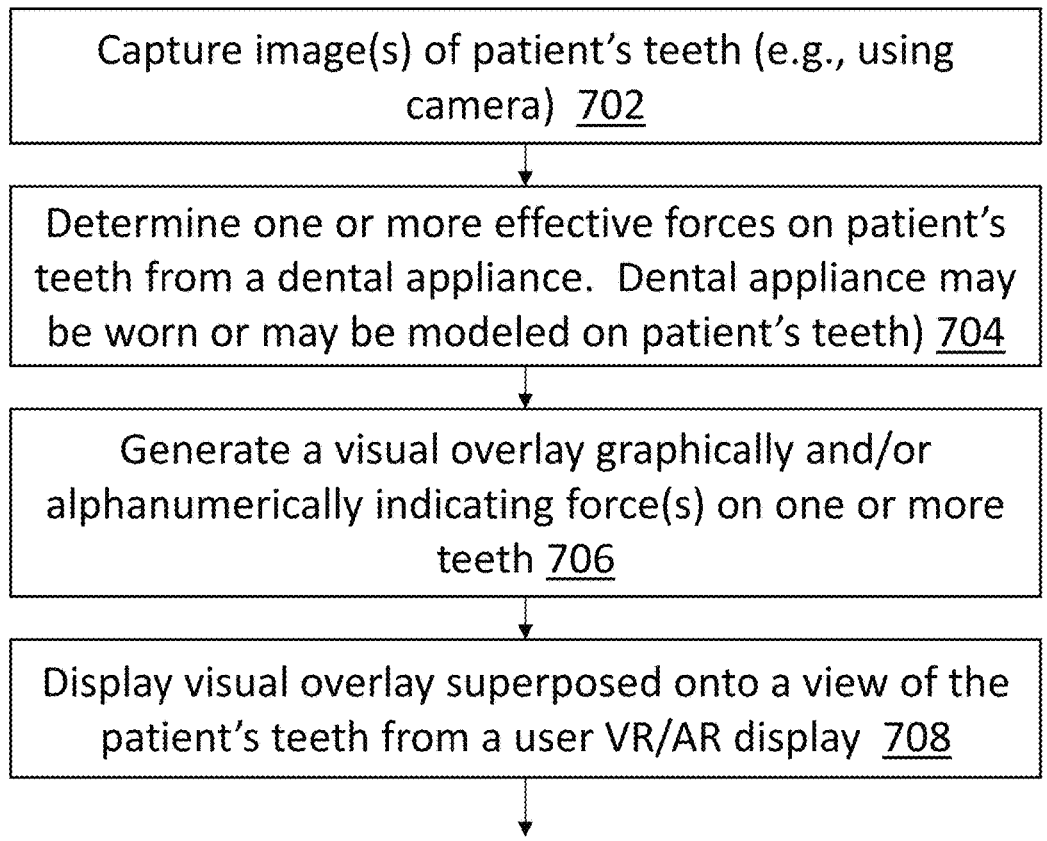
FIG. 7 is a flowchart describing the use of an AR system to display forces on a patient's teeth from an orthodontic appliance.

FIG. 7 is a flowchart describing the use of an AR system to display forces on a patient's teeth from an orthodontic appliance. At step 702 of the flowchart, the AR system can capture one or more images of the patient's teeth with a dental appliance on the teeth. The dental appliance can include, for example, elastic bands or wire based dental appliances that attach to two or more different locations in a patient's jaw. Referring to FIG. 1A, camera(s) 179 of the image capture subsystem 160 can capture 2D or 3D images of the patient's teeth. These images can be stored in data store 110 as image data 135.

Next, at step 704 of the flowchart, the AR system can determine one or more forces on the patient's teeth from the dental appliance. The forces can be identified with the feature recognition processing 124 of FIG. 1A, which can evaluate the dental appliance and process the forces applied by the dental appliance to the patient's teeth. The feature recognition processing 124 can use the image data 135, reference data 138, and patient data 140 to evaluate these forces. In some examples, the feature recognition processing 124 can identify the length and/or angle of elastic bands or wires in the patient's mouth, and calculate the forces applied by the elastic bands or wires to the patient's teeth.

At step 706 of the flowchart, the AR system can generate a visual overlay that graphically and/or alphanumerically indicates the forces on the patient's teeth. The visual overlay can comprise outlines, shading, coloring, force vectors, or alphanumerical data, etc. For example, in a patient with an elastic band attached to two teeth, the visual overlay can provide detailed information on the forces applied to each of the patient's teeth as a result of the elastic band. Furthermore, in some examples, the visual overlay can also include an indication if the forces applied by the dental appliance to the patient's teeth exceed a force threshold. This can indicate to a user that the dental appliance is improperly applying more force to the teeth than is desired. Referring to FIG. 1A, display control 118 of the processor 108 can generate the visual overlay from the reference data 138 and image data 135.

At step 708 of the flowchart, the visual overlay from step 706 can be displayed onto an AR display of the AR system. A user of the AR display, such as a physician, can view the patient's teeth and dental appliance along with the visual overlay that graphically or alphanumerically indicates the forces on the patient's teeth. Referring to FIG. 1A, display control 118 of the processor 108 can generate the visual overlay from the reference data 138 and image data 135 and display the visual overlay onto the AR display 150.

Figure 8:
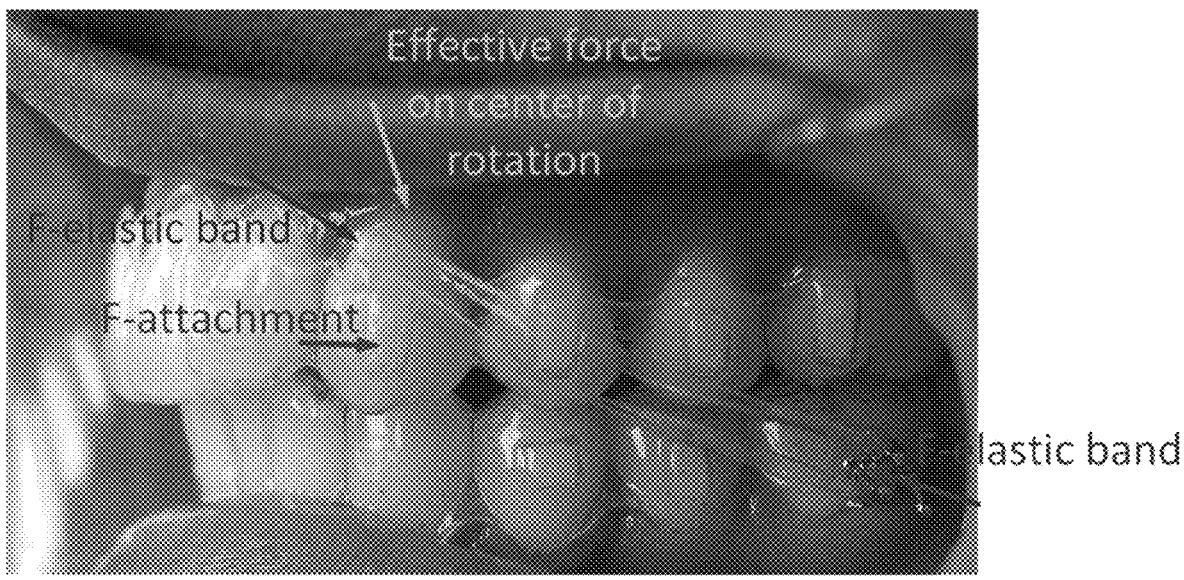
FIG. 8 illustrates examples of what the elastic bands forces visual overlay of FIG. 7 may look like from the user's perspective.
Figure 9:
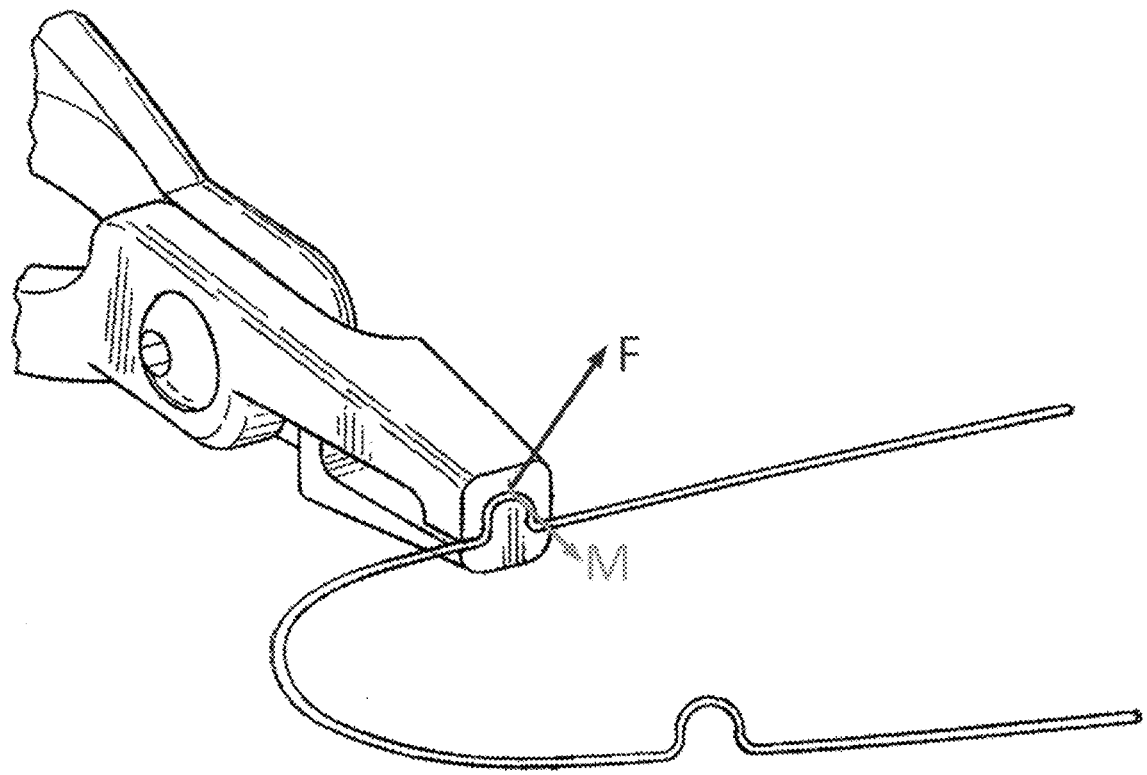
FIG. 9 shows what the metal wire forces visual overlay of FIG. 7 may look like from the user's perspective.

FIG. 8 illustrates examples of what the elastic bands forces visual overlay of FIG. 7 may look like from the user's perspective. FIG. 9 shows what the metal wire forces visual overlay of FIG. 7 may look like from the user's perspective. For example, the forces may be indicated with a visual marker, outline, color, alphanumeric values, or force vectors to indicate the forces applied by the dental appliance to the patient's teeth, and whether they surpass a force threshold.

Figure 10A:
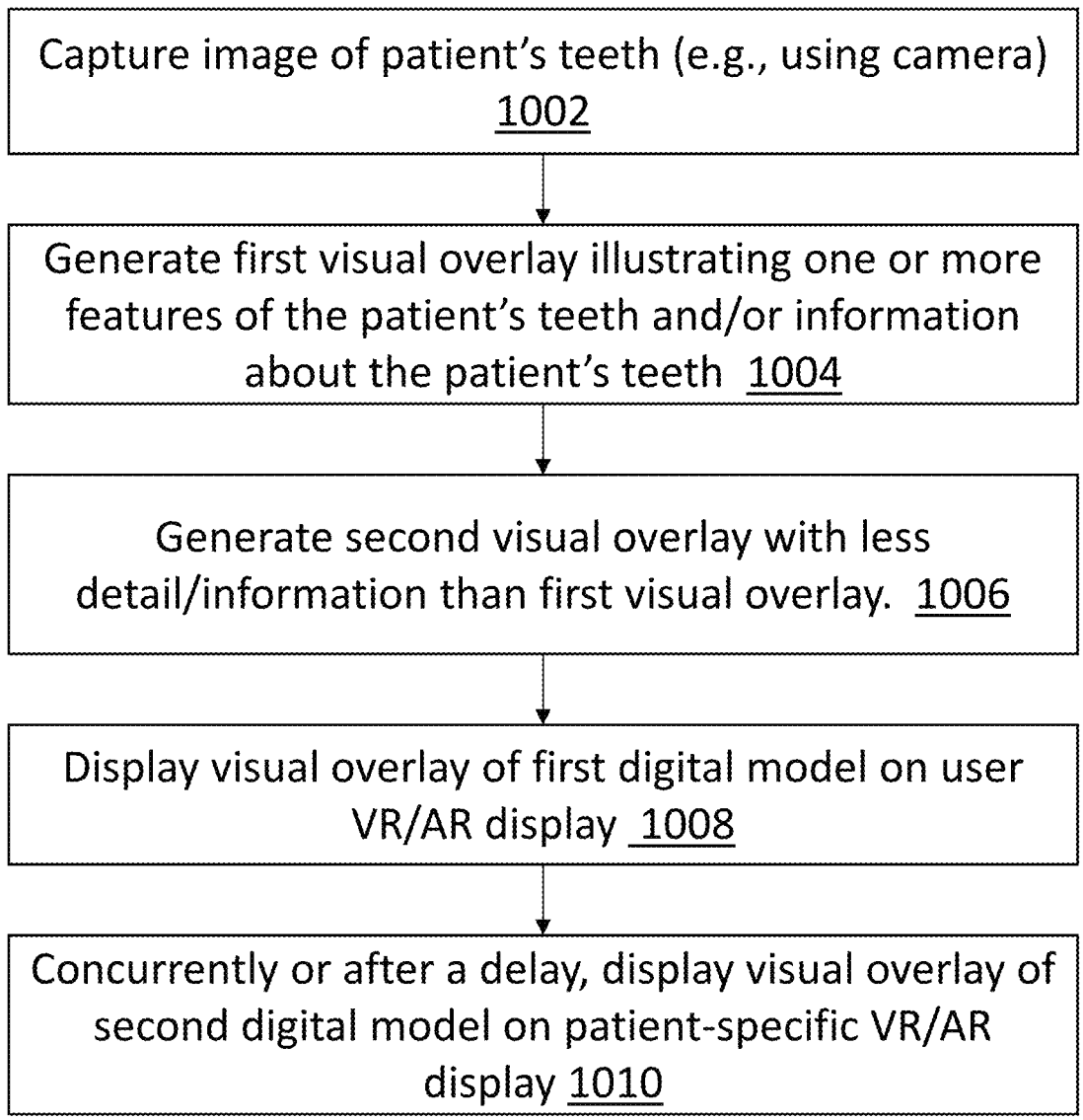
FIG. 10A is a flowchart describing the use of an AR system to dental information to a physician and a patient.

FIG. 10A is a flowchart describing the use of an AR system to dental information to a physician and a patient. At step 1002 of the flowchart, the AR system can capture one or more images of the patient's teeth. The patient can be wearing a dental appliance during the image capture, or can be preparing for a new dental appliance. Referring to FIG. 1A, camera(s) 179 of the image capture subsystem 160 can capture 2D or 3D images of the patient's teeth. These images can be stored in data store 110 as image data 135.

Next, at step 1004 of the flowchart, the AR system can generate a first visual overlay that illustrates one or more features of the patient's teeth or provides information about the patient's teeth or dental appliance. The visual overlay can comprise any of the visual overlays described above, including virtual models of the patient's teeth, error conditions with fitment of a dental appliance, attachment points on a patient's teeth, force applied by a dental appliance to the patient's teeth, etc. Furthermore, as described above, the visual overlay can include outlines, shading, coloring, force vectors, or alphanumerical data, etc. The first visual overlay can be tailored with the type of information that would be useful to a practitioner, such as a physician or orthodontist. Referring to FIG. 1A, display control 118 of the processor 108 can generate the visual overlay from the reference data 138 and image data 135.

At step 1006 of the flowchart, the AR system can generate a second visual overlay that includes less detail/information than the first overlay of step 1004. The second visual overlay can be tailored with the type of information that would be useful to a patient. For example, technical information such as force vectors and advanced treatment planning would not be included in the second visual overlay. However, the second visual overlay may be used to show a patient what their teeth will look like after treatment, or to show a patient specific issues with their teeth or their current dental appliance.

At step 1008 of the flowchart, the visual overlay from step 1004 can be displayed onto a user AR display of the AR system. The user display is reserved for a physician or practitioner who can view the patient's teeth and dental appliance along with the visual overlay. Referring to FIG. 1A, display control 118 of the processor 108 can generate the visual overlay from the reference data 138 and image data 135 and display the visual overlay onto the AR display 150.

At step 1010 of the flowchart, the visual overlay from step 1006 can be displayed onto a patient specific AR or VR display of the AR system. The patient specific display is reserved for the patient, who can view the less detailed visual overlay while being evaluated by the user. The second visual overlay can be a useful tool for the user to explain the treatment plan and/or procedure to the patient. Referring to FIG. 1A, display control 118 of the processor 108 can generate the visual overlay from the reference data 138 and image data 135 and display the visual overlay onto the AR display 150.

Figure 10B:
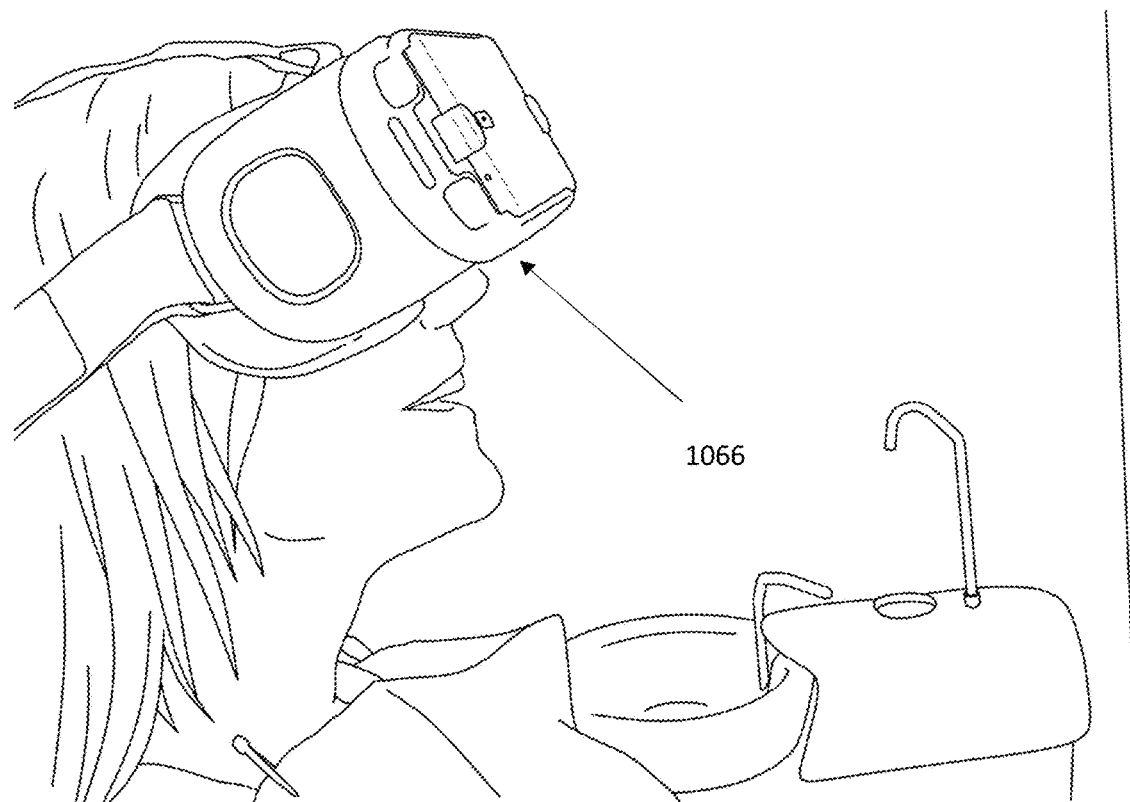
FIG. 10B shows an example of a patient wearing a slave patient-wearable display device (e.g., VR device) that may be controlled by a master dental professional-wearable AR device, as shown in FIG. 10C.
Figure 10C:
FIG. 10C is an illustration of a master/slave AR/VR system in which the dental professional wears an AR display device that may provide augmented information overlaid onto the view of the patient's dentition, while the patient is shown a virtual reality view including the perspective seen by the dental professional (the AR view) onto which all or a subset of the information displayed to the dental professional from the AR view is overlaid.

FIGS. 10B and 10C illustrate an example of an AR (and/or combined AR/VR) system including a master/slave relationship. In this example, the patient may watch what the dental professional is seeing on the AR system worn by the dental professional. The dental professional may show the patient one or more features that the dental professional may want to explain. For example, if the dental professional touches a tooth, the patient's screen can zoom on that particular tooth and show what the dental professional wants to explain. As shown in FIG. 10B, the patient may wear a patient display 1066 and the dental professional may wear an AR device including a display and one or more cameras.

Examples of planning and fabrication of orthodontic aligners, including elastic polymeric positioning appliances, are described, e.g., in U.S. Pat. No. 5,975,893, and in published PCT application WO 98/58596, which is herein incorporated by reference for all purposes.

The diagram of FIG. 1 shows an example of an AR system 100. The system components may be modular, e.g., may include one or more modules (sub-portions) of the AR system that may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Data stores can be implemented, for example, as software embodied in a physical computer-readable medium on a specific-purpose machine, in firmware, in hardware, in a combination thereof, or in an applicable known or convenient device or system. Data store-associated components, such as database interfaces, can be considered "part of" a data store, part of some other system component, or a combination thereof, though the physical location and other characteristics of data store-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based data store is a data store that is compatible with cloud-based computing systems and engines.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of evaluating an orthodontic treatment, the method comprising:
   capturing, with a processor of an augmented reality device, image data of a patient's teeth with an elastic band or wire on the patient's teeth;
   determining, from the image data, with the processor, a length and/or angle of the elastic band or wire and one or more effective forces on the patient's teeth when a dental appliance is applied to the patient's teeth, wherein the one or more effective forces includes an effective force on a center of rotation of at least one of the patient's teeth resulting from the elastic band or wire;
   generating a visual overlay graphically illustrating the one or more effective forces; and
   outputting the visual overlay to a display of the augmented reality device, wherein the visual overlay is superimposed over a view of the patient's teeth and of the dental appliance placed on the patient's teeth.

2. The method of claim 1, wherein generating the visual overlay comprises representing the one or more effective forces as an arrow.

3. The method of claim 1, wherein generating the visual overlay comprises representing the one or more effective forces as an alphanumeric value.

4. The method of claim 1, wherein generating the visual overlay comprises representing the one or more effective forces as a color.

5. The method of claim 1, wherein determining the one or more effective forces on the patient's teeth comprises determining a moment or torque on one or more teeth.

6. The method of claim 1, wherein capturing the image data of the patient's teeth comprises capturing the image data of the patient's teeth when the dental appliance is worn by the patient.

7. The method of claim 1, wherein capturing the image data of the patient's teeth comprises capturing the image data of the patient's teeth when the dental appliance is not being worn by the patient; further comprising receiving a virtual model of the dental appliance.

8. A system comprising:
   an augmented reality display;
   one or more processors; and
   a memory coupled to the one or more processors, the memory configured to store computer-program instructions, that, when executed by the one or more processors,
   perform a computer-implemented method comprising:
      capturing, with a processor of an augmented reality device, image data of a patient's teeth and of an elastic band or wire placed on the patient's teeth;
      determining from the image data, with the processor, a length and/or angle of the elastic band or wire, and an effective force on a center of rotation of at least one of the patient's teeth resulting from the elastic band or wire;
      generating, with the processor, a visual overlay identifying the effective force; and
      outputting the visual overlay to a display of the augmented reality device, wherein the visual overlay is superimposed over a view of the patient's teeth and of the elastic band or wire placed on the patient's teeth.

9. The system of claim 8, wherein generating the visual overlay comprises representing the effective force as an arrow.

10. The system of claim 8, wherein generating the visual overlay comprises representing the effective force as an alphanumeric value.

11. The system of claim 8, wherein generating the visual overlay comprises representing the effective force as a color.

12. The system of claim 8, wherein determining the effective force comprises determining a moment or torque on one or more teeth.

13. The system of claim 8, wherein capturing the image data of the patient's teeth comprises capturing the image data of the patient's teeth when a dental appliance is worn by the patient.

14. The system of claim 8, wherein capturing the image data of the patient's teeth comprises capturing the image data of the patient's teeth when a dental appliance is not being worn by the patient; further comprising receiving a virtual model of the dental appliance.

15. The system of claim 8, wherein outputting the visual overlay comprises displaying estimated forces acting on the patient's teeth where the estimated forces exceed a threshold value, wherein the threshold value is based on poor fit results in high forces acting on the patient's teeth and/or an improperly placed band or attachment.

16. A method of evaluating an orthodontic treatment, the method comprising:
- capturing, with a processor of an augmented reality device, image data of a patient's teeth and of an elastic band or wire placed on the patient's teeth;
- determining from the image data, with the processor, a length and/or angle of the elastic band or wire, and an effective force on a center of rotation of at least one of the patient's teeth resulting from the elastic band or wire;
- generating, with the processor, a visual overlay identifying the effective force; and
- outputting the visual overlay to a display of the augmented reality device, wherein the visual overlay is superimposed over a view of the patient's teeth and of the elastic band or wire placed on the patient's teeth.

17. The method of claim 16, wherein generating the visual overlay comprises representing the effective force as a vector.

18. The method of claim 16, wherein generating the visual overlay comprises representing the effective force as a color.

19. The method of claim 16, wherein capturing the image data of the patient's teeth comprises capturing the image data of the patient's teeth when a dental appliance is worn by the patient.

20. The method of claim 16, wherein capturing the image data of the patient's teeth comprises capturing the image data of the patient's teeth when a dental appliance is not being worn by the patient; further comprising receiving a virtual model of the dental appliance.

* * * * *